United States Patent
Dai et al.

(10) Patent No.: US 11,124,512 B2
(45) Date of Patent: Sep. 21, 2021

(54) COMPOUND, DISPLAY PANEL AND DISPLAY APPARATUS

(71) Applicant: Xiamen Tianma Micro-Electronics Co., Ltd., Xiamen (CN)

(72) Inventors: Wenpeng Dai, Shanghai (CN); Wei Gao, Shanghai (CN); Jinghua Niu, Shanghai (CN); Lei Zhang, Shanghai (CN)

(73) Assignee: XIAMEN TIANMA MICRO-ELECTRONICS CO., LTD., Xiamen (CN)

( * ) Notice: Subject to any disclaimer, the term of this patent is extended or adjusted under 35 U.S.C. 154(b) by 0 days.

(21) Appl. No.: 16/810,865

(22) Filed: Mar. 6, 2020

(65) Prior Publication Data

US 2020/0207767 A1   Jul. 2, 2020

(30) Foreign Application Priority Data

Dec. 31, 2019 (CN) .......................... 201911411163.8

(51) Int. Cl.
  *C07D 471/06* (2006.01)
  *H01L 51/52* (2006.01)
  *C07D 519/00* (2006.01)

(52) U.S. Cl.
  CPC ......... *C07D 471/06* (2013.01); *C07D 519/00* (2013.01); *H01L 51/5237* (2013.01)

(58) Field of Classification Search
  None
  See application file for complete search history.

(56) References Cited

FOREIGN PATENT DOCUMENTS

| CN | 103319695 A | 9/2013 |
| CN | 110256428 A | 9/2019 |
| JP | 1988-151958 A | 6/1988 |
| JP | 2016178060 A | 10/2016 |
| KR | 20140083189 A | 7/2014 |

OTHER PUBLICATIONS

Liu et al. "Three pyrido[2,3,4,5-lmn]phenanthridine derivatives and their large band gap copolymers for organic solar cells" Journal of Materials Chemistry A, 2014, 321-325.*
Han et al. "Synthesis, Characterization, and Properties of Diazapyrenes via Bischler-Napieralski Reaction" Journal of Organic Chemistry, 2019, vol. 84, No. 7, pp. 3953-3959.*
Office Action of Chinese Patent Application No. 201911411163.8 dated Aug. 24, 2020.

* cited by examiner

*Primary Examiner* — Joseph R Kosack
(74) *Attorney, Agent, or Firm* — Kilpatrick Townsend & Stockton

(57) ABSTRACT

The present disclosure provides an azapyrene compound, a display panel and a display apparatus. The compound has a structure represented by Chemical Formula 1, in which $X_1$-$X_4$ are each a nitrogen atom or C—$R_a$, one or two of $X_1$-$X_4$ are a nitrogen atom; only one of $X_1$ and $X_2$ is a nitrogen atom; only one of $X_3$ and $X_4$ is N; $R_a$ is mainly hydrogen, deuterium, or C1-C10 alkyl; $Ar_1$ and $Ar_2$ are each C6-C30 aryl or C3-C30 heteroaryl; m and n are 0, 1, 2, or 3, and when one of m and n is 0, the other one of m and n is not 0; and $L_1$ and $L_2$ are a single bond, C6-C30 arylene, or C3-C30 heteroarylene; p and q are 0, 1, or 2. The compound can be used as a CPL material to improve external quantum efficiency (EQE) of an organic light-emitting device and light-emitting efficiency.

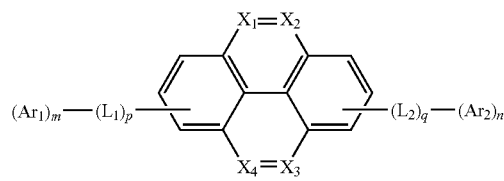

14 Claims, 2 Drawing Sheets

COMPOUND, DISPLAY PANEL AND DISPLAY APPARATUS

CROSS-REFERENCE TO RELATED DISCLOSURES

The present application claims priority to Chinese Patent Application No. 201911411163.8, filed on Dec. 31, 2019, the content of which is incorporated herein by reference in its entirety.

FIELD

The present disclosure relates to the field of organic electroluminescent materials, and particularly, to an azapyrene compound, a display panel including the azapyrene compound, and a display apparatus.

BACKGROUND

Organic light-emitting diodes (OLEDs) have made great progress with decades of development. Although the internal quantum efficiency of OLEDs is close to 100%, the external quantum efficiency is only about 20%. Most of the light emitted by OLED is confined within the light-emitting device due to factors such as substrate mode loss, surface plasma loss, and waveguide effects, thereby resulting in a great energy loss.

In top emission devices, an organic cover layer (Capping Layer, CPL) is deposited on a translucent metal aluminum electrode to adjust an optical interference distance, suppress external light reflection, and suppress extinction caused by surface plasma energy movement, thereby improving a light extraction efficiency and a light-emitting efficiency of OLED devices.

SUMMARY

In view of the problems in the related art, a first embodiment of the present disclosure provides a compound having a structure represented by Chemical Formula 1:

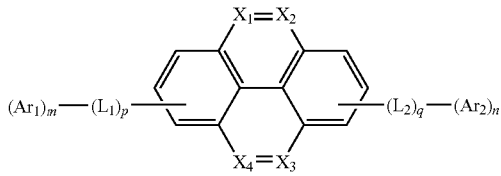

Chemical Formula 1 wherein $X_1$-$X_4$ are each independently a nitrogen atom or C—$R_a$,
one or two of $X_1$-$X_4$ are a nitrogen atom,
when one of $X_1$ and $X_2$ is a nitrogen atom, the other one of $X_1$ and $X_2$ is not N;
when one of $X_3$ and $X_4$ is a nitrogen atom, the other one of $X_3$ and $X_4$ is not N;
$R_a$ is selected from the group consisting of hydrogen, deuterium, fluorine, a substituted or unsubstituted C1-C20 alkyl, a substituted or unsubstituted C1-C20 alkoxy, a substituted or unsubstituted C1-C20 thioalkyl, a substituted or unsubstituted C6-C30 aryl, and a substituted or unsubstituted C3-C30 heteroaryl;
$R_a$ is present independently or forms, with adjacent carbon atoms, a substituted or unsubstituted aliphatic ring, a substituted or unsubstituted aromatic ring, or a substituted or unsubstituted heteroaromatic ring;
$Ar_1$ and $Ar_2$ are each independently selected from the group consisting of a substituted or unsubstituted C6-C30 aryl, and a substituted or unsubstituted C3-C30 heteroaryl;
m and n are each an integer independently selected from 0, 1, 2, or 3, and when one of m and n is 0, the other one of m and n is not 0;
$L_1$ and $L_2$ are each independently a single bond, a substituted or unsubstituted C6-C30 arylene, or a substituted or unsubstituted C3-C30 heteroarylene; and
p and q are each an integer independently selected from 0, 1, or 2.

A second embodiment of the prevent disclosure provides a display panel, including an organic light-emitting device. The organic light-emitting device includes an anode, a cathode arranged opposite to the anode, a capping layer located a side of the cathode facing away from the anode, and an organic layer located between the anode and the cathode, the capping layer includes the compound according to the first embodiment of the present disclosure.

A third embodiment of the prevent disclosure provides a display apparatus including the display panel according to the second embodiment of the present disclosure.

DESCRIPTION OF EMBODIMENTS

Figure 1:
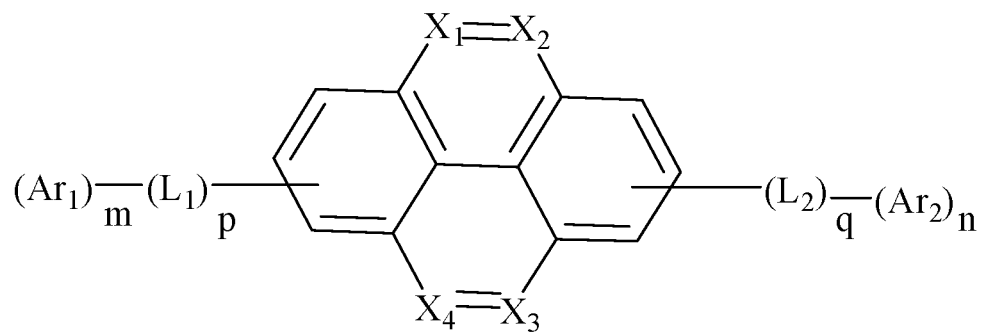
FIG. 1 is a chemical formula of a compound provided by an embodiment of the present disclosure.

The present disclosure is further described through examples and comparative examples. These examples are merely used to illustrate the present disclosure, but the present disclosure is not limited to the following examples. Any modification or equivalent replacement to the embodiments of the present disclosure without departing from the embodiments of the present disclosure should fall within the protection scope of the present disclosure.

The first embodiment of the present disclosure provides a compound having a structure represented by Chemical Formula 1:

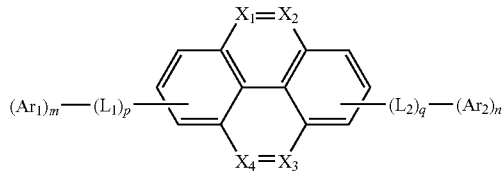

Chemical Formula 1 wherein $X_1$-$X_4$ are each independently a nitrogen atom or C—$R_a$,
one or two of $X_1$-$X_4$ are a nitrogen atom, when one of X₁ and X₂ is a nitrogen atom, the other one of X₁ and X₂ is not N;
when one of X₃ and X₄ is a nitrogen atom, the other one of X₃ and X₄ is not N;
R_a is selected from the group consisting of hydrogen, deuterium, fluorine, a substituted or unsubstituted C1-C20 alkyl, a substituted or unsubstituted C1-C20 alkoxy, a substituted or unsubstituted C1-C20 thioalkyl, a substituted or unsubstituted C6-C30 aryl, and a substituted or unsubstituted C3-C30 heteroaryl;
R_a is present independently or forms, with adjacent carbon atoms, a substituted or unsubstituted aliphatic ring, a substituted or unsubstituted aromatic ring, or a substituted or unsubstituted heteroaromatic ring;
Ar₁ and Ar₂ are each independently selected from the group consisting of a substituted or unsubstituted C6-C30 aryl, and a substituted or unsubstituted C3-C30 heteroaryl;
m and n are each an integer independently selected from 0, 1, 2, or 3, and when one of m and n is 0, the other one of m and n is not 0;
L₁ and L₂ are each independently a single bond, a substituted or unsubstituted C6-C30 arylene, or a substituted or unsubstituted C3-C30 heteroarylene; and
p and q are each an integer independently selected from 0, 1, or 2.

The compound of the present disclosure a high refractive index, and thus can be used as a material of a CPL (capping layer) of an organic light-emitting device to effectively improve the external quantum efficiency (EQE) of the organic light-emitting device. In addition, the compound of the present disclosure has a small extinction coefficient in a blue light wavelength range (400 nm to 450 nm), and has almost no absorption of blue light, which is conducive to improving light-emitting efficiency.

In an embodiment of the compound of the present disclosure, each of X₁ and X₃ is a nitrogen atom, and each of X₂ and X₄ is C—R_a; or each of X₁ and X₄ is a nitrogen atom, and each of X₂ and X₃ is C—R_a, where R_a is H.

In the present embodiment, nitrogen atoms are located at para-positions of azapyrene, which avoids the potential thermal instability of the azo structure and the absorption of visible light by the azo structure. Therefore, the azopyrene compound of the present disclosure is suitable to be used as the material of the optical capping layer (CPL).

In an embodiment of the compound of the present disclosure, each of X₁ and X₃ is a nitrogen atom, and each of X₂ and X₄ is C—R_a; or each of X₁ and X₄ is N, and each of X₂ and X₃ is C—R_a, where R_a is methyl. In the present embodiment, except the good stability and zero absorption of visible light, the compound can be easily synthesized by the presence of methyl group, because there are abundant raw materials including methyl group and intermediate synthesis is also relatively easy.

In an embodiment of the compound of the present disclosure, Ar₁ and Ar₂ are each independently selected from the group consisting of a substituted or unsubstituted phenyl, a substituted or unsubstituted biphenyl, a substituted or unsubstituted triphenyl, a substituted or unsubstituted tetraphenyl, a substituted or unsubstituted naphthyl, a substituted or unsubstituted anthryl, a substituted or unsubstituted phenanthryl, a substituted or unsubstituted pyrenyl, a substituted or unsubstituted fluorenyl, a substituted or unsubstituted spirobifluorenyl, a substituted or unsubstituted carbazolyl, a substituted or unsubstituted dibenzofuryl, a substituted or unsubstituted dibenzothienyl, a substituted or unsubstituted pyridinyl, a substituted or unsubstituted triazinyl, a substituted or unsubstituted indolocarbazolyl, a substituted or unsubstituted indolobenzofuryl, a substituted or unsubstituted indolobenzothienyl, a substituted or unsubstituted benzofurylpyrimidinyl, and a substituted or unsubstituted benzothienylpyrimidinyl.

In another embodiment of the compound of the present disclosure, the substituted or unsubstituted phenyl is o-biphenyl, m-biphenyl, or p-biphenyl; the substituted or unsubstituted biphenyl is o-triphenyl, m-triphenyl, or p-triphenyl; the substituted or unsubstituted triphenyl is o-tetraphenyl, m-tetraphenyl, or p-tetraphenyl; the substituted or unsubstituted fluorenyl is 1-fluorenyl, 2-fluorenyl, 3-fluorenyl, or 4-fluorenyl; the substituted or unsubstituted spirobifluorenyl is 1-spirobifluorenyl, 2-spirobifluorenyl, 3-spirobifluorenyl, or 4-spirobifluorenyl; the substituted or unsubstituted naphthyl is 1-naphthyl or 2-naphthyl; the substituted or unsubstituted carbazolyl is 1-carbazolyl, 2-carbazolyl, 3-carbazolyl, or 4-carbazolyl; and the substituted or unsubstituted dibenzofuryl is 1-dibenzofuryl, 2-dibenzofuryl, 3-dibenzofuryl, or 4-dibenzofuryl; the substituted or unsubstituted dibenzothienyl is 1-dibenzothienyl, 2-dibenzothienyl, 3-dibenzothienyl, or 4-dibenzothienyl; the substituted or unsubstituted pyridyl is 2-pyridyl, 3-pyridyl, or 4-pyridyl; and the substituted or unsubstituted pyrimidinyl is 2-pyrimidinyl, 4-pyrimidinyl, or 5-pyrimidinyl.

In an embodiment of the compound of the present disclosure, Ar₁ and Ar₂ are each independently selected from the group consisting of phenyl, biphenyl, triphenyl, tetraphenyl, fluorenyl, spirobifluorenyl, naphthyl, pyrrolyl, furyl, thienyl, indolyl, benzofuryl, benzothienyl, carbazolyl, dibenzofuryl, dibenzothienyl, indenocarbazolyl, indolocarbazolyl, pyridyl, pyrimidinyl, pyrazinyl, pyridazinyl, triazinyl, phenanthryl, triphenylenyl, and combinaitons thereof.

In an embodiment of the compound of the present disclosure, Ar₁ and Ar₂ are each independently selected from the group consisting of naphthyl, anthryl, phenanthryl, and pyrenyl, and L₁ and L₂ are each a single bond.

In an embodiment of the compound of the present disclosure, the compound is any one of the following compounds:

P1
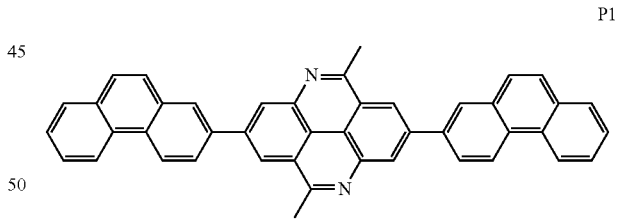

P2
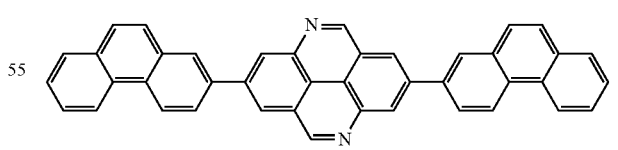

P3
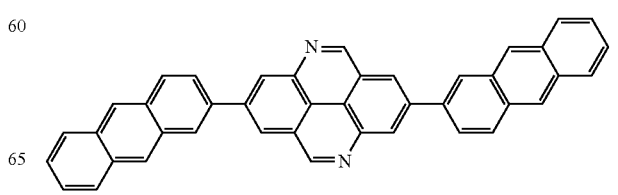

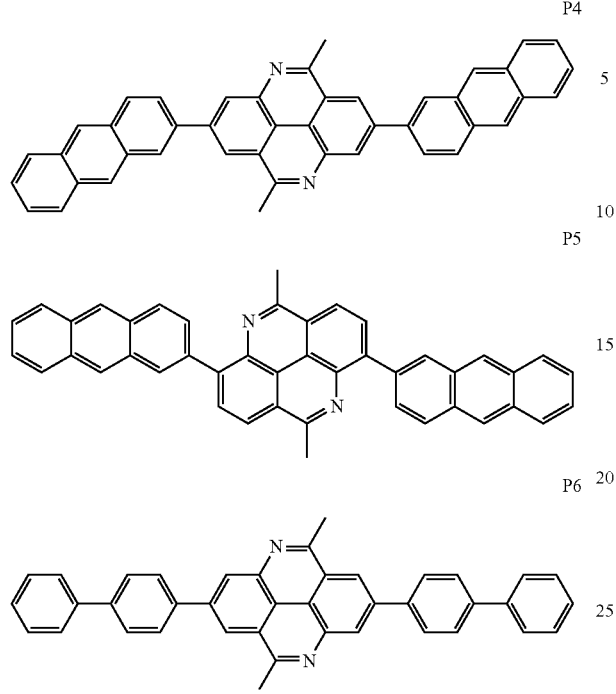
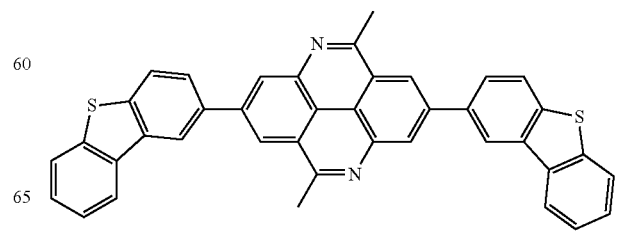

P16
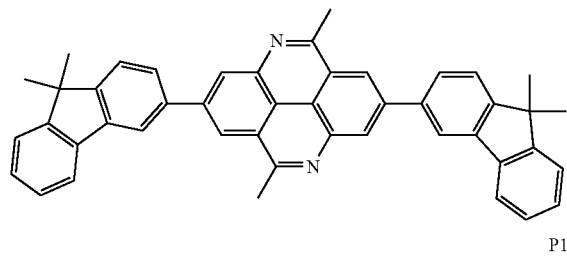
P17
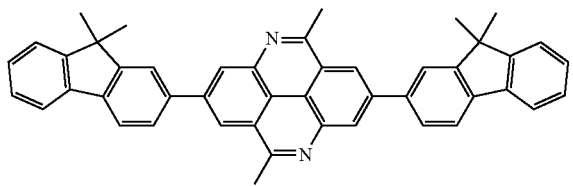
P18
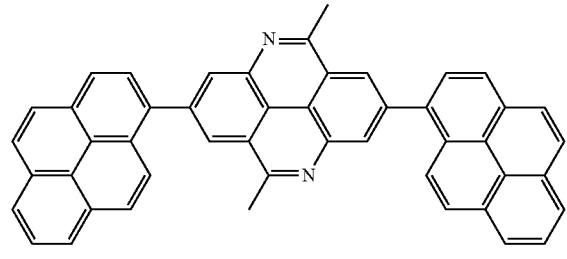
P19
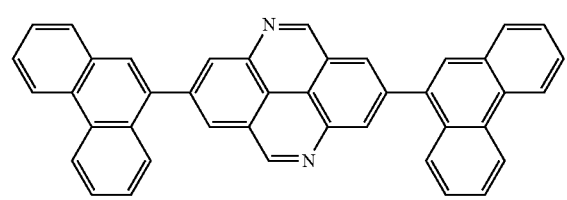
P20
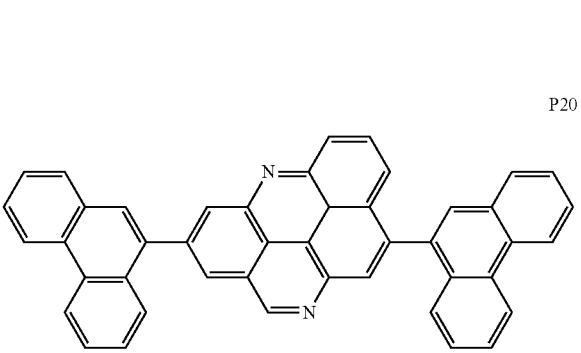
P21
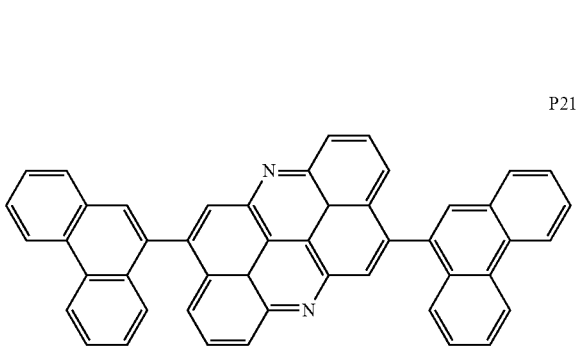
P22
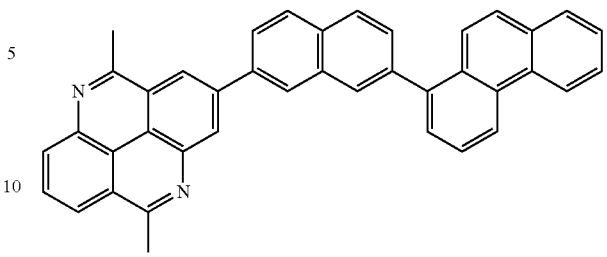
P23
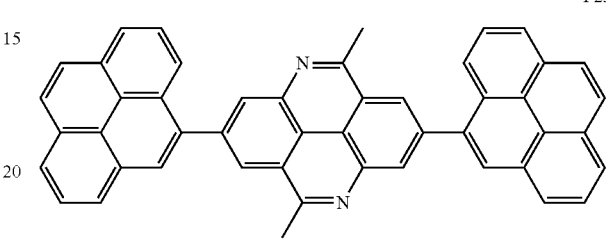
P24
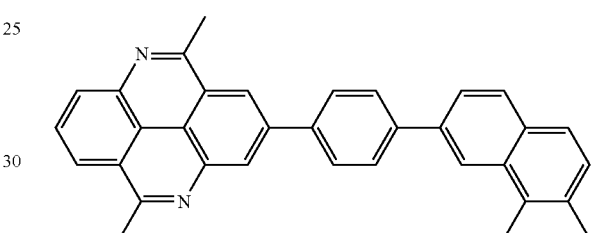
P25
P26
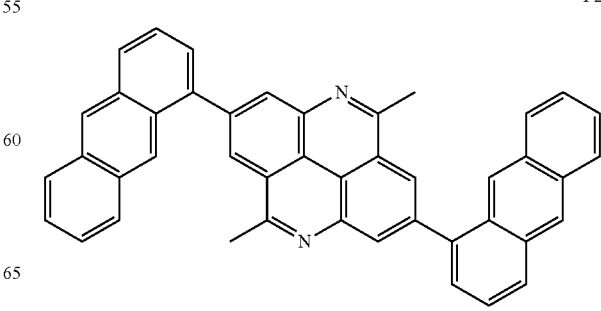

-continued
P27
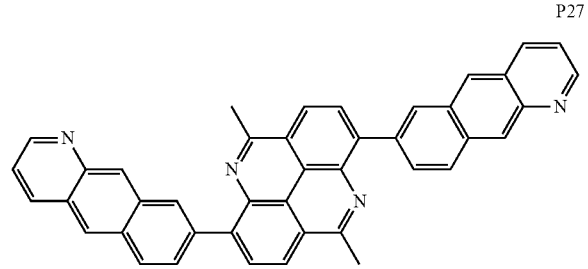
P28
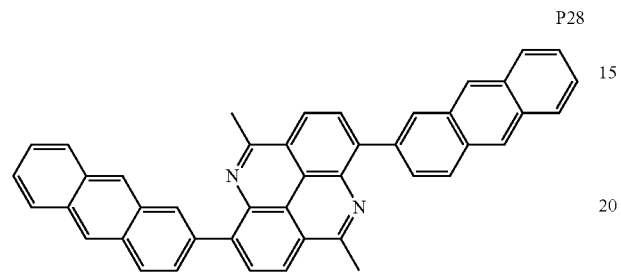
P29
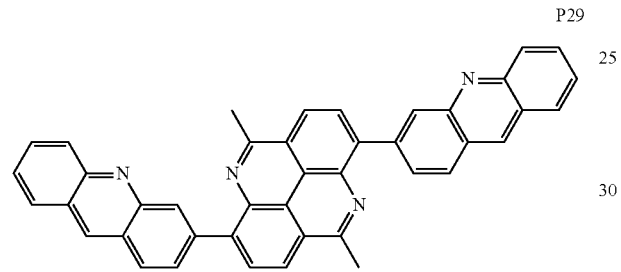
P30
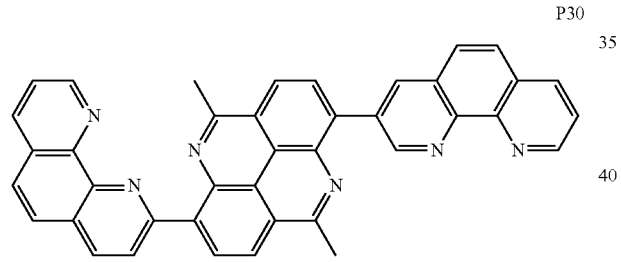
P31
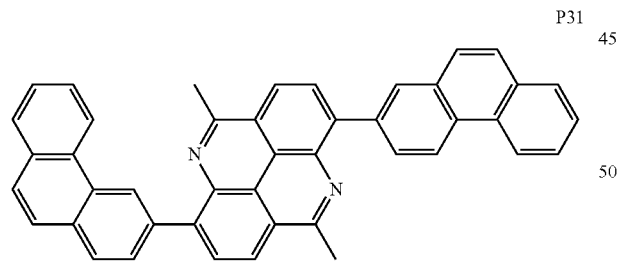
P32
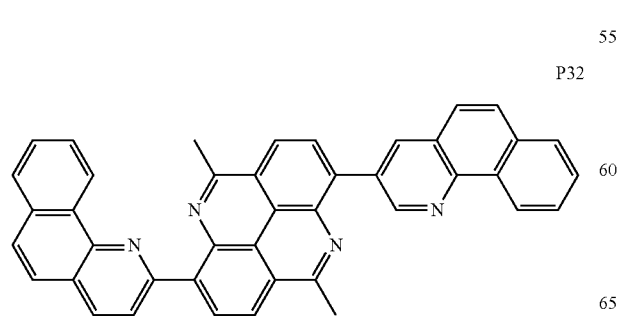
-continued
P33
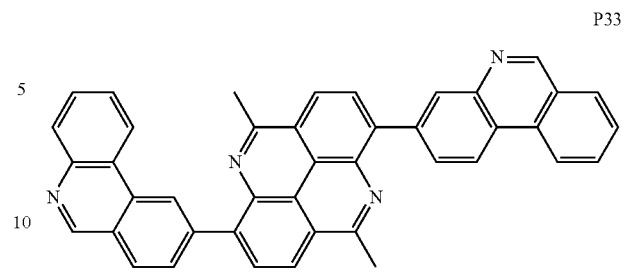
P34
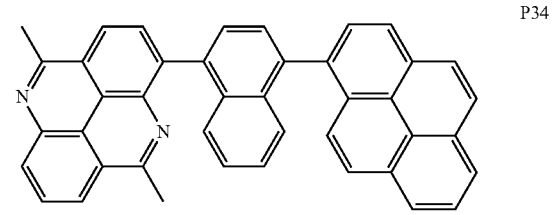
P35
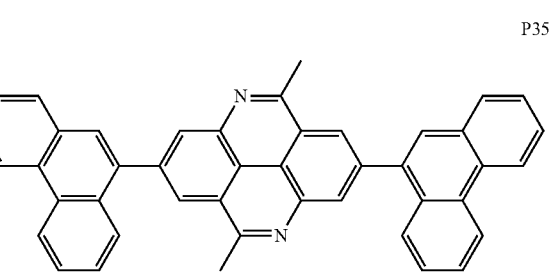
P36
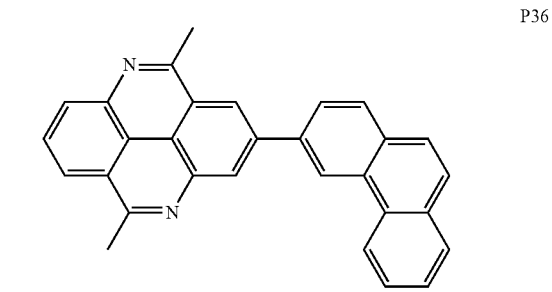
P37
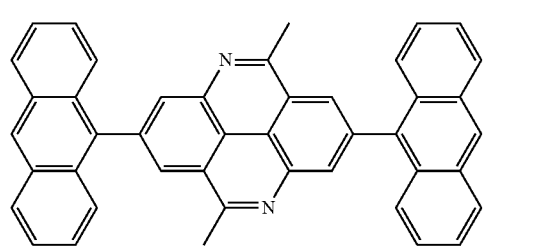
P38
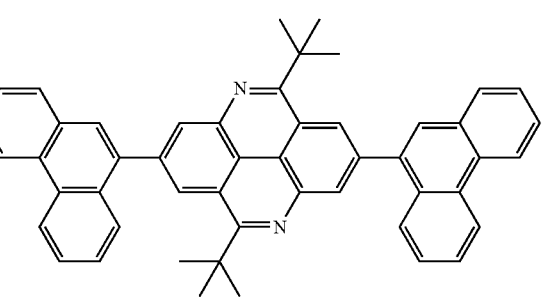

-continued

P39 P40 P41 P42 P43 P44 P45 P46 P47 P48 P49 P50

P51
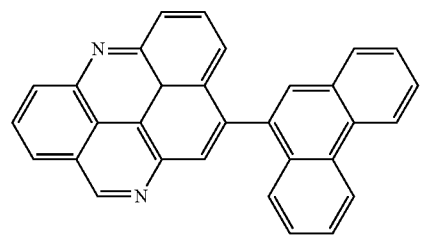
P52
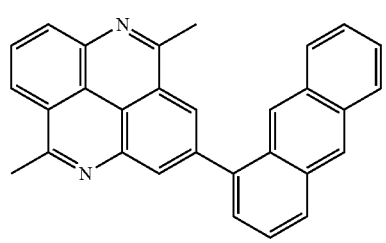
P53
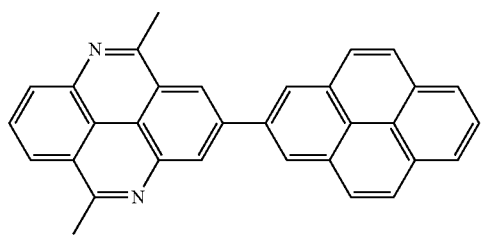
P54
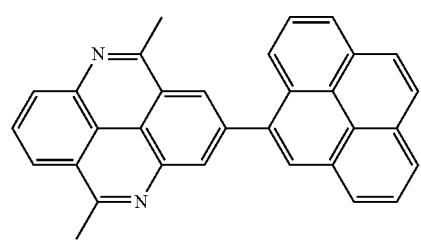
P55
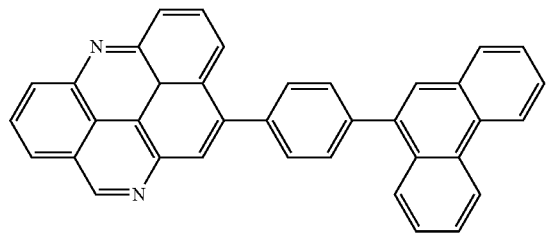
P56
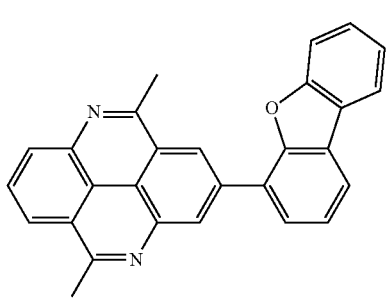
P57
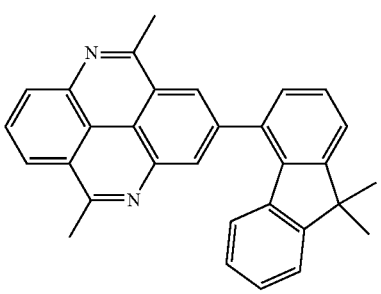
P58
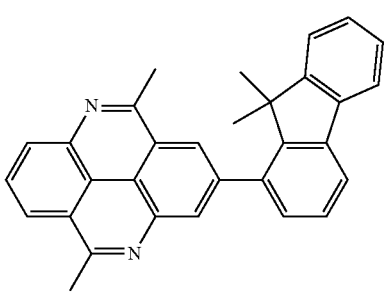
P59
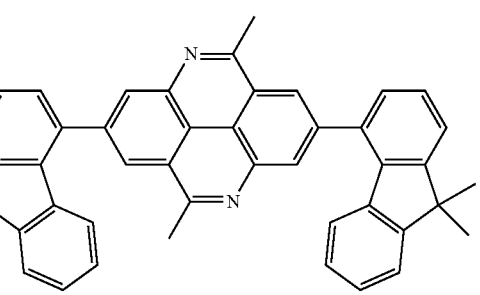
P60
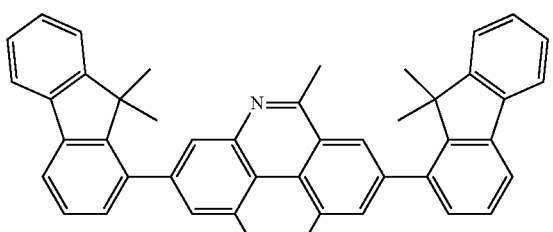
P61
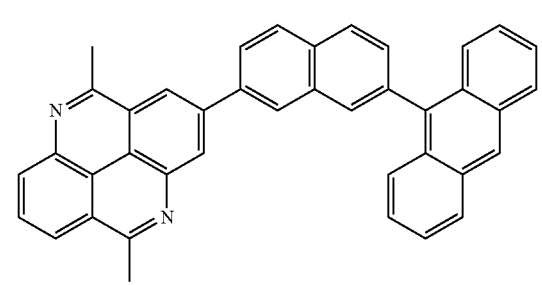

P62
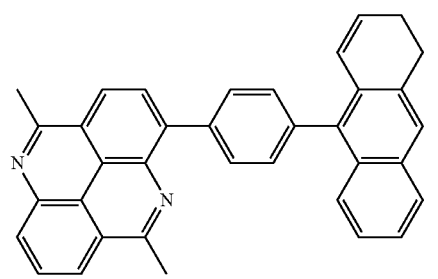
P63
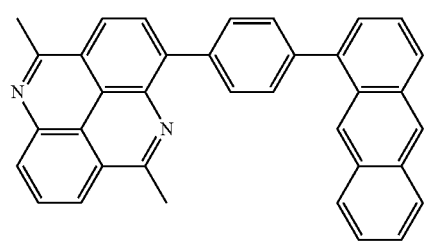
P64
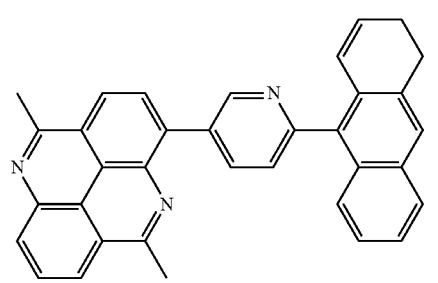
P65
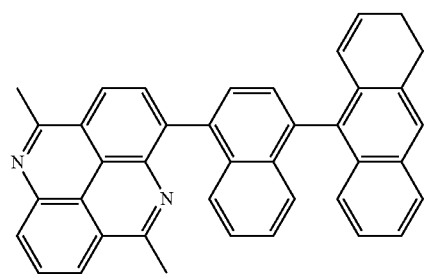
P66
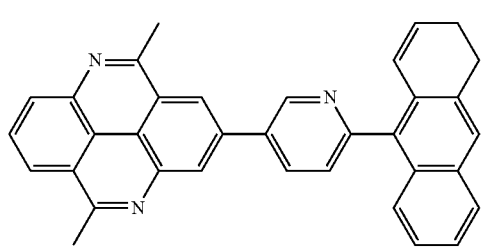
P67
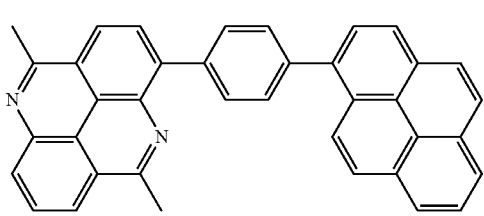
P68
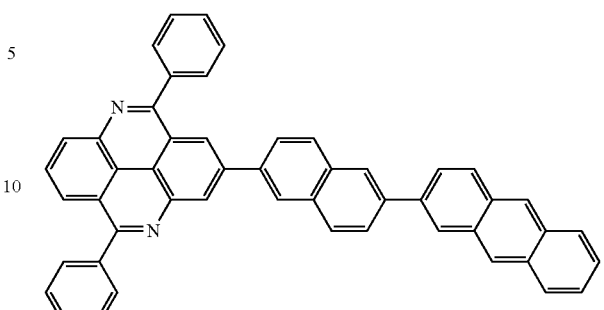
P69
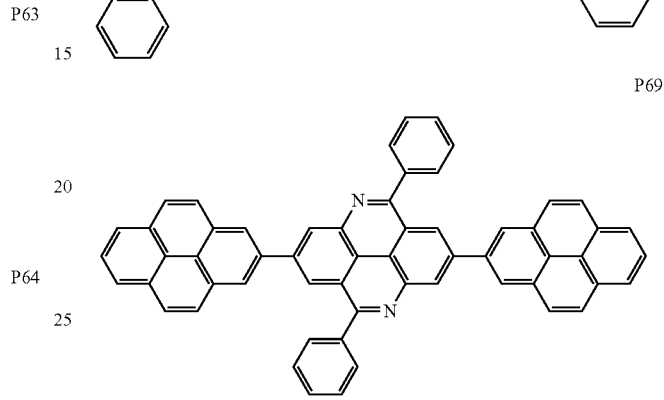
P70
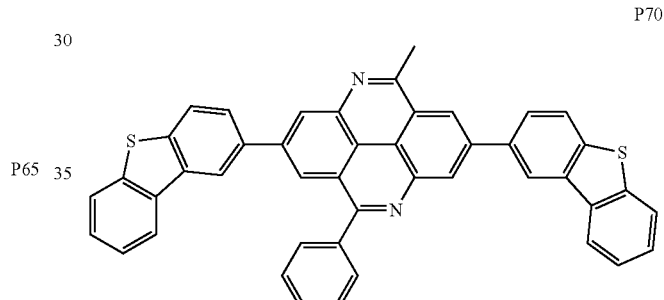
P71
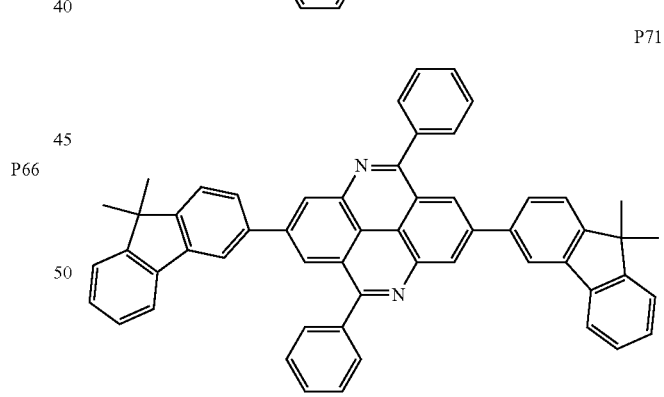
P72
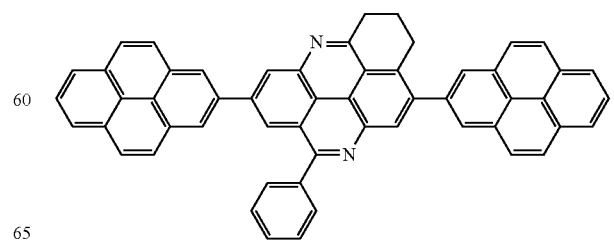

-continued

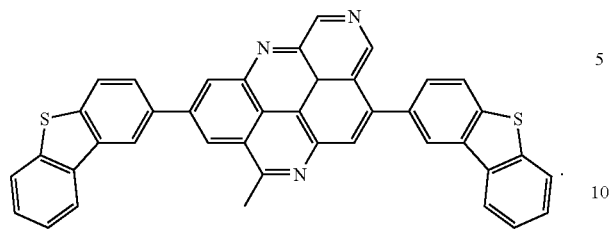

P73

The compound of the present disclosure has a refractive index greater than or equal to 2.0 for visible light having a wavelength of 400 nm to 700 nm. The compound having the refractive index greater than or equal to 2.0 satisfies the basic performance requirements on the CPL material of OLED devices, and thus the compound is suitable to be used as the CPL material.

The compound of the present disclosure has an extinction coefficient smaller than or equal to 0.05 for visible light having a wavelength of 400 nm to 450 nm. That is, the compound of the present disclosure has a small extinction coefficient in the blue light wavelength range, such that the organic light-emitting device adopting the azapyrene compound of the present disclosure as the capping layer material has higher light-emitting efficiency.

Another embodiment of the present disclosure provides a display panel including an organic light-emitting device. The organic light-emitting device includes an anode, a cathode opposite to the anode, a capping layer located a side of the cathode facing away from the anode, and an organic layer located between the anode and the cathode. The capping layer includes the azapyrene compound of the present disclosure.

In the display panel of the present disclosure, the cathode together with the capping layer have a transmittance greater than or equal to 65% for visible light having a wavelength of 400 nm to 700 nm.

The synthesis schemes of several exemplary compounds of the present disclosure are listed below. The overall synthetic scheme of the compound of the present disclosure is shown below.

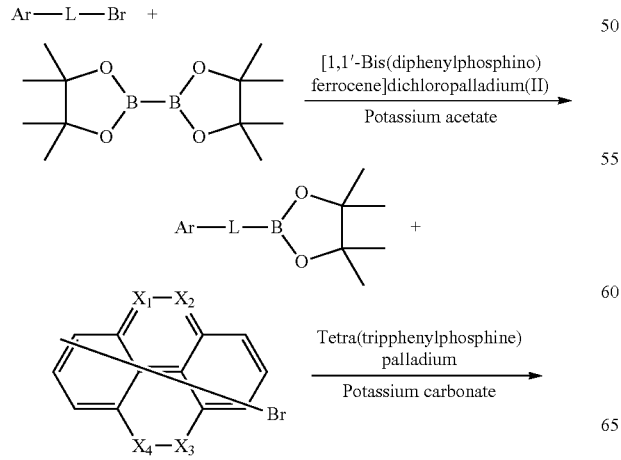

-continued

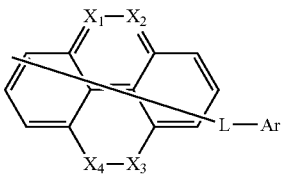

Example 1

Synthesis of Compound P1

The synthesis scheme is as below:

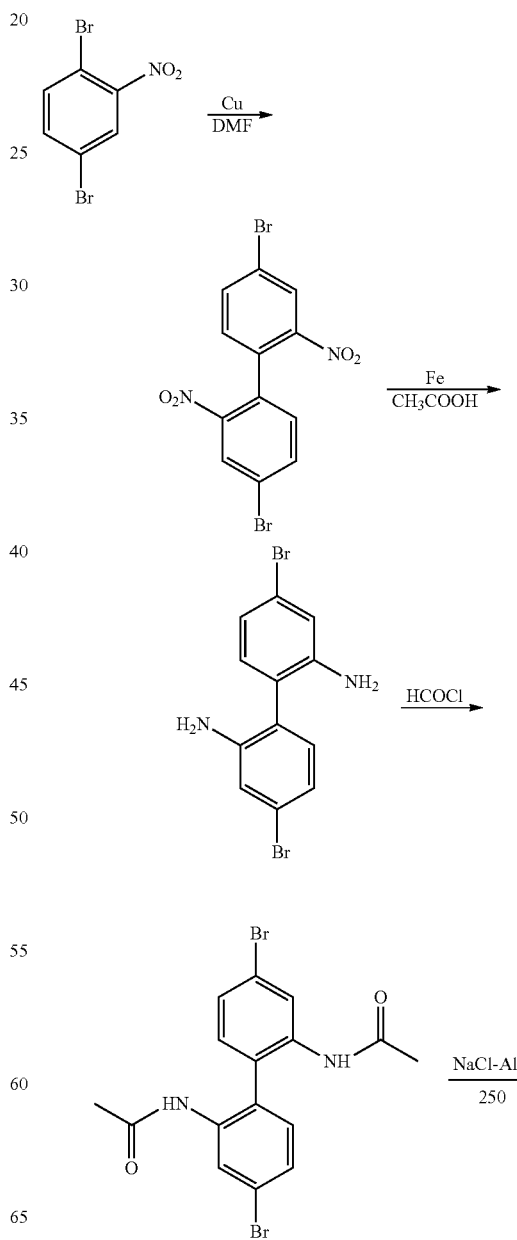

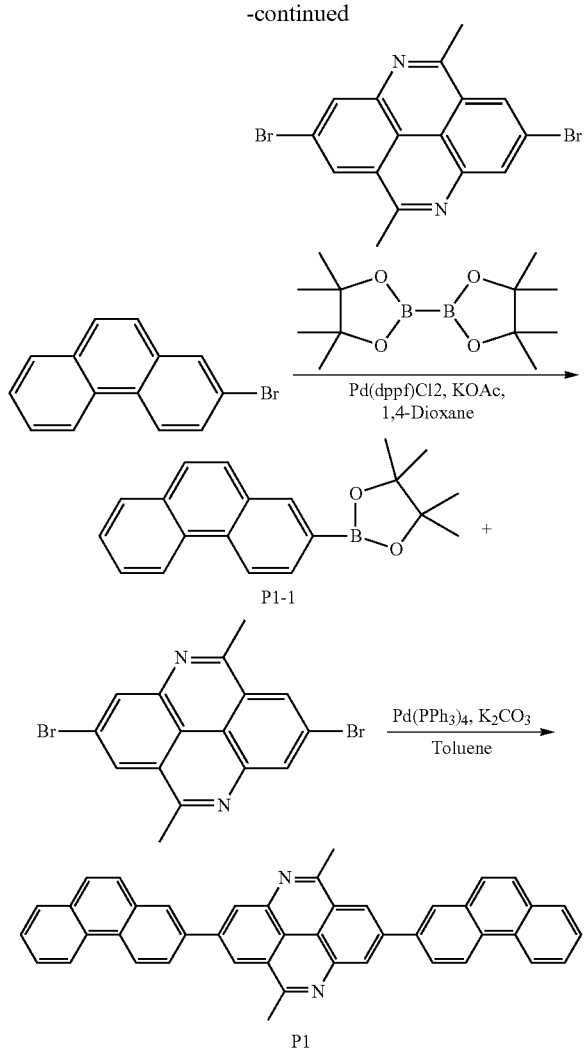

(1) In a 250 ml round bottom flask, 2,5-dibromonitrobenzene (15 mmol) and Cu (7 mmol) were added to dry DMF (100 ml), and the reaction was performed at 125° C. for 3.5 hours under nitrogen atmosphere. The obtained intermediate mixture solution was added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate product 4,4-dibromo-2,2-dinitrobenzene.

(2) In a 250 ml round bottom flask, 4,4-dibromo-2,2-dinitrobenzene (15 mmol) and Fe (0.225 mol) were added to dry acetic acid (100 ml), and the reaction was performed at 80° C. for 1 h under nitrogen atmosphere. The obtained intermediate mixture solution was directly filtered to remove the metal residue, as a reaction solution for the next reaction.

(3) In a 250 ml round bottom flask, acetyl chloride (75 mmol), the reaction solution obtained from the previous step, and triethylamine (5 ml) were added to dry dichloromethane (100 ml), and reacted at 0° C. overnight under nitrogen atmosphere. The obtained intermediate was added to water, then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate product N-(2'-acetamido-4,4'-dibromobiphen-2-yl)-acetamide.

(4) In a 250 ml round-bottomed flask, N-(2'-acetamino-4,4'-dibromobiphen-2-yl)-acetamide (15 mmol), aluminum chloride, and sodium chloride (0.15 mol) were carefully added. The reaction was performed at 250° C. for 8 h under nitrogen atmosphere. The obtained intermediate was added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate 2,2'-dimethyl-4,4'-dibromophenanthridine.

(5) 2-bromophenanthrene (15 mmol), potassium acetate (40 mmol), dry 1,4-dioxane (60 ml), Pd(dppf)Cl$_2$ (0.4 mmol), and bis(pinacolato)diboron (50 mmol) were mixed in a 250 ml round bottom flask and stirred at 90° C. for 48 h under nitrogen atmosphere. The obtained intermediate was cooled to room temperature, added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate product P1-1.

(6) In a 250 ml round bottom flask, P1-1 (20 mmol), 2,2'-dimethyl-4,4'-dibromophenanthridine (10 mmol) and Pd(PPh$_3$)$_4$ (0.3 mmol) were added to a mixture of toluene (30 ml)/ethanol (20 ml) and an aqueous solution (10 ml) of potassium carbonate (12 mmol), and the mixture was refluxed under nitrogen atmosphere for 12 h. The obtained mixture was cooled to room temperature, then added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain the final product P1.

Characterization results of compound P1:

$^1$H NMR (400 MHz, CDCl$_3$) δ 8.99-8.34 (m, 6H), 8.27 (s, 2H), 8.12-7.71 (m, 12H), 7.65 (s, 2H), 2.55 (s, 6H);

Deviceal analysis results (molecular formula: C$_{44}$H$_{28}$N$_2$): theoretical: C, 90.41; H, 4.79; N, 4.80; measured: C, 90.21; H, 4.80; N, 4.97. ESI-MS(m/z)(M+) obtained through Liquid Chromatography/Mass Spectrometry: theoretical, 584.23; measured, 584.02.

Example 2

Synthesis of Compound P4

The synthesis scheme of compound P4 is shown as below:

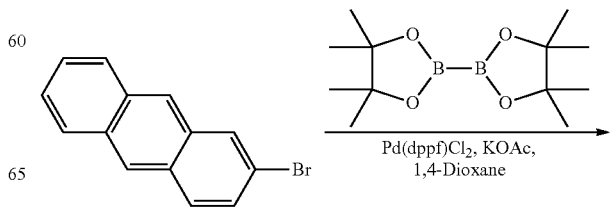

-continued

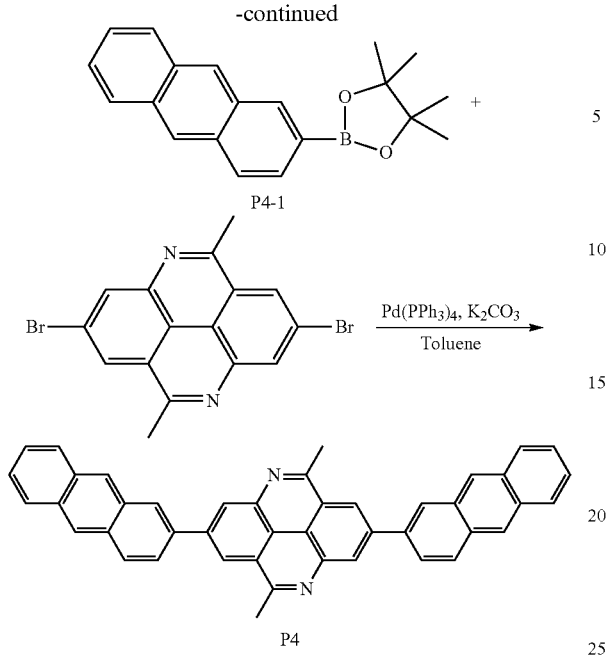

(1) In a 250 ml round bottom flask, the intermediate 2-bromoanthracene (15 mmol) and potassium acetate (40 mmol) were mixed with dry 1,4-dioxane (60 ml), Pd(dppf)Cl$_2$ (0.4 mmol), and bis(pinacolato)diboron (50 mmol), and the mixture was stirred under nitrogen atmosphere at 90° C. for 48 hours. The obtained intermediate was cooled to room temperature, added to water, and then filtered through a diatomite pad. The filtrate was extracted with dichloromethane, then washed with water, and dried with anhydrous magnesium sulfate. After filtration and evaporation, the crude product was purified by silica gel column chromatography to obtain an intermediate product P4-1.

(2) In a 250 ml round bottom flask, the intermediate P4-1 (20 mmol), 2,2'-dimethyl-4,4'-dibromophenanthridine (10 mmol) and Pd(PPh$_3$)$_4$ (0.3 mmol) were added to a mixture of toluene (30 ml)/ethanol (20 ml) and an aqueous solution (10 ml) of potassium carbonate (12 mmol), and refluxed under nitrogen atmosphere for 12 h. The obtained mixture was cooled to room temperature, added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain the final product P4.

Characterization results of compound P4:

$^1$H NMR (400 MHz, CDCl$_3$) δ 8.31 (s, 4H), 8.27 (s, 2H), 8.13 (s, 2H), 7.97-7.39 (m, 12H), 7.65 (s, 2H), 2.55 (s, 6H);

Deviceal analysis results (molecular formula: C$_{44}$H$_{28}$N$_2$): theoretical: C, 90.41; H, 4.79; N, 4.80; measured: C, 90.38; H, 4.80; N, 4.81. ESI-MS(m/z)(M+) obtained through Liquid Chromatography/Mass Spectrometry: theoretical, 584.23; measured, 584.42.

Example 3

Synthesis of Compound P29

The synthesis scheme of compound P29 is shown as below:

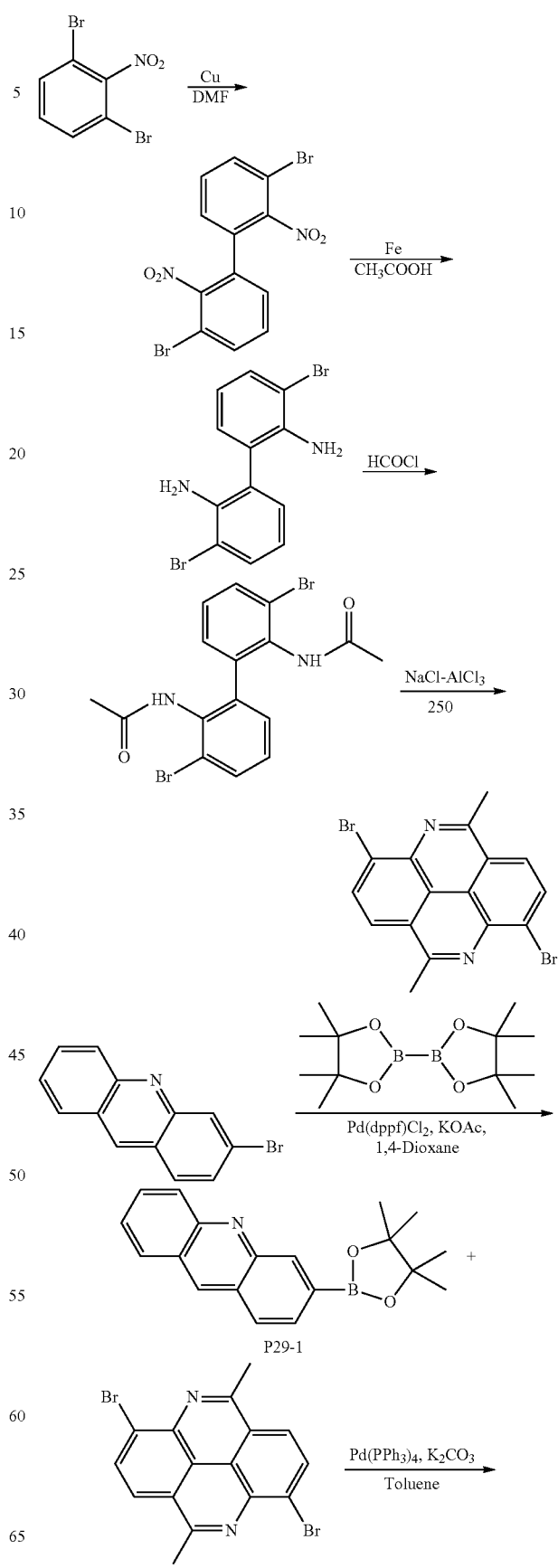

-continued

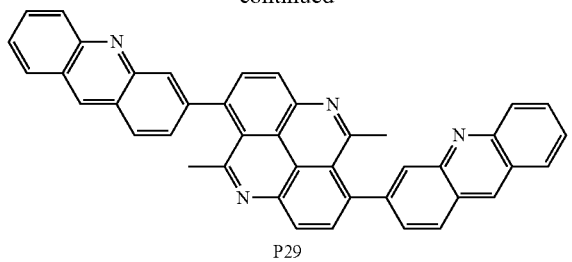

P29

(1) In a 250 ml round bottom flask, 1,3-dibromonitrobenzene (15 mmol) and Cu (7 mmol) were added to dry DMF (100 ml), and reacted at 125° C. for 3.5 hours under nitrogen atmosphere. The obtained intermediate mixture solution was added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate 3,3'-dibromo-2,2'-dinitrobenzene.

(2) In a 250 ml round bottom flask, 3,3'-dibromo-2,2'-dinitrobenzene (15 mmol) and Fe (0.225 mol) were added to dry acetic acid (100 ml), and reacted at 80° C. for 1 h under nitrogen atmosphere. The obtained intermediate mixture solution was directly filtered to remove the metal residue, and used as a reaction solution for the next reaction.

(3) In a 250 ml round bottom flask, acetyl chloride (75 mmol), the reaction solution from the previous step, and triethylamine (5 ml) were added to dry dichloromethane (100 ml), and reacted at 0° C. overnight under nitrogen atmosphere. The obtained intermediate was added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain an intermediate product N-(2'-acetamido-3,3'-dibromobiphen-2-yl)-acetamide.

(4) In a 250 ml round bottom flask, N-(2'-acetamino-3,3'-dibromobiphen-2-yl)-acetamide (15 mmol) was carefully added to aluminum chloride and sodium chloride (0.15 mol), and reacted at 250° C. for 8 hours under nitrogen atmosphere. The obtained intermediate was added to water, and then filtered through a diatomite pad. The filtrate was extracted with dichloromethane, then wash with water, and dried over anhydrous magnesium sulfate. After filtration and evaporation, the crude product was purified by silica gel column chromatography to obtain an intermediate 2,2'-dimethyl-3,3'-dibromophenanthridine.

(5) In a 250 ml round bottom flask, 3-bromoacridine (15 mmol) and potassium acetate (40 mmol) were mixed with dry 1,4-dioxane (60 ml), Pd(dppf)Cl$_2$ (0.4 mmol) and bis(pinacolato)diboron (50 mmol), and the mixture was stirred at 90° C. for 48 hours under nitrogen atmosphere. The obtained intermediate was cooled to room temperature, added to water, and then filtered through a diatomite pad. The filtrate was extracted with dichloromethane, then washed with water, and dried with anhydrous magnesium sulfate. After filtration and evaporation, the crude product was purified by silica gel column chromatography to obtain an intermediate product P29-1.

(6) In a 250 ml round bottom flask, the intermediate product P29-1 (20 mmol), 2,2'-dimethyl-3,3'-dibromophenanthridine (10 mmol) and Pd(PPh$_3$)$_4$ (0.3 mmol) were added to a mixture of toluene (30 ml)/ethanol (20 ml) and an aqueous solution (10 ml) of potassium carbonate (12 mmol), and then refluxed for 12 h under nitrogen atmosphere. The obtained mixture was cooled to room temperature, added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain the final product P29.

Characterization results of compound P29:
$^1$H NMR (400 MHz, CDCl$_3$) δ 8.27 (s, 2H), 8.00 (s, 2H), 7.74-7.61 (m, 12H), 7.83 (d, J=8.4 Hz, 2H), 7.49 (d, J=8.4 Hz, 2H), 2.55 (s, 6H).

Deviceal analysis results (molecular formula: C$_{42}$H$_{26}$N$_4$): theoretical: C, 86.01; H, 4.44; N, 9.55; measured: C, 86.00; H, 4.34; N, 9.65. ESI-MS(m/z)(M+) obtained through Liquid Chromatography/Mass Spectrometry: theoretical, 586.22; measured, 586.53.

Example 4

Synthesis of Compound P43

The synthesis scheme of compound P43 is shown as below:

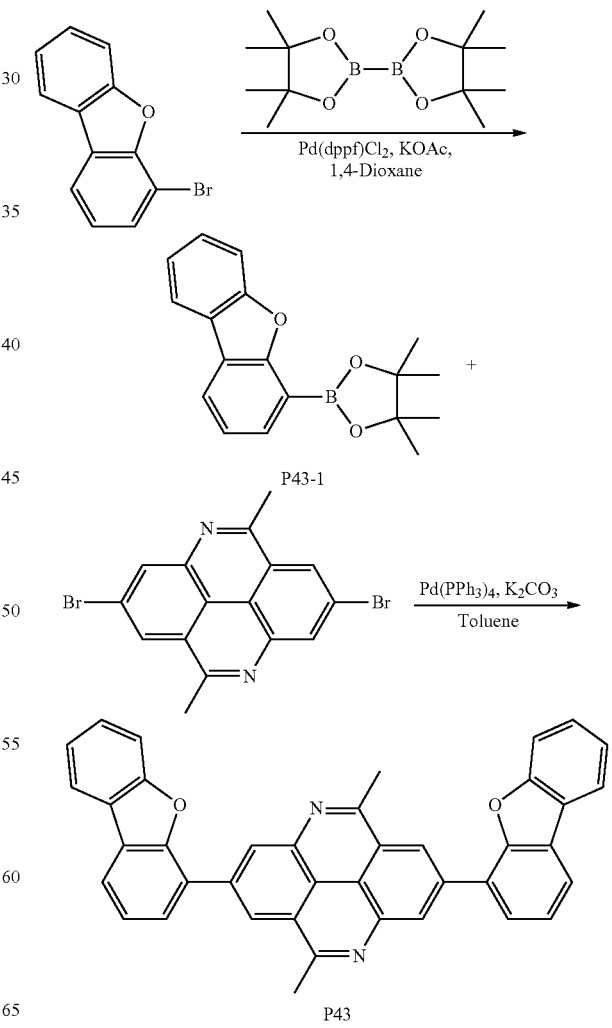

(1) In a 250 ml round bottom flask, the intermediate 4-bromodibenzofuryl (15 mmol) and potassium acetate (40 mmol) were mixed with dry 1,4-dioxane (60 ml), Pd(dppf)Cl$_2$ (0.4 mmol), and bis(pinacolato)diboron (50 mmol), and the mixture was stirred at 90° C. for 48 hours under nitrogen atmosphere. The obtained intermediate was cooled to room temperature, added to water, and then filtered through a diatomite pad. The filtrate was extracted with dichloromethane, then washed with water, and dried with anhydrous magnesium sulfate. After filtration and evaporation, the crude product was purified by silica gel column chromatography to obtain an intermediate product P43-1.

(2) In a 250 ml round bottom flask, the intermediate product P43-1 (20 mmol), 2,2'-dimethyl-4,4'-dibromophenanthridine (10 mmol) and Pd(PPh$_3$)$_4$ (0.3 mmol) were added to a mixture of toluene (30 ml)/ethanol (20 ml) and an aqueous solution (10 ml) of potassium carbonate (12 mmol), and refluxed for 12 h under nitrogen atmosphere. The obtained mixture was cooled to room temperature, added to water, and then filtered through a diatomite pad. The filtrate was extracted with dichloromethane, then washed with water, and dried over anhydrous magnesium sulfate. After filtration and evaporation, the crude product was purified by silica gel column chromatography to obtain the final product P43.

Characterization results of compound P43:

$^1$H NMR (400 MHz, CDCl$_3$) δ 8.27 (s, 2H), 7.65 (s, 2H), 7.49 (d, J=8.4 Hz, 4H), 7.42 (d, J=8.4 Hz, 2H), 7.40-7.19 (m, 8H), 2.55 (s, 6H).

Deviceal analysis results (molecular formula: C$_{40}$H$_{24}$N$_2$O2): theoretical: C, 85.11; H, 4.26; N, 4.96; 0, 5.67; measured: C, 85.10; H, 4.23; N, 4.95; 0, 5.73. ESI-MS(m/z)(M+) obtained through Liquid Chromatography/Mass Spectrometry: theoretical, 564.18; measured, 564.37.

Figure 2:
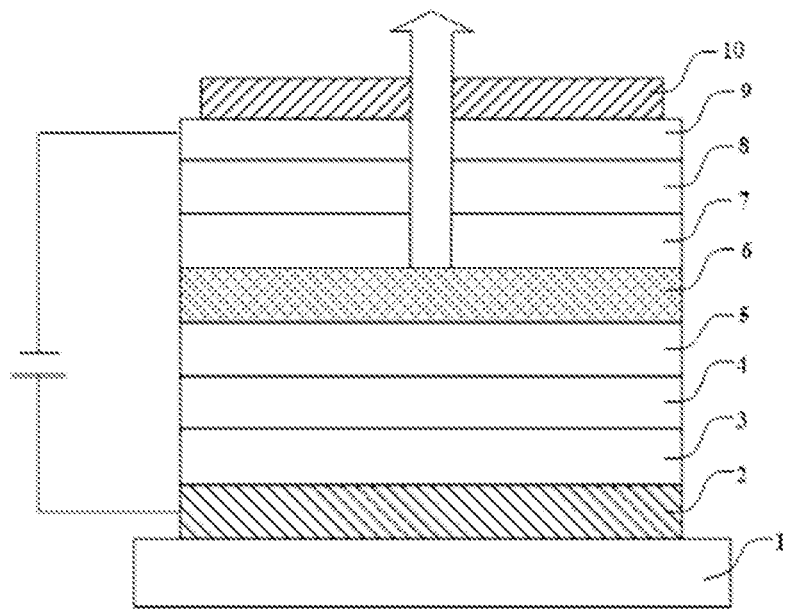
FIG. 2 is a structural schematic diagram of an OLED device according to an embodiment of the present disclosure.

Another embodiment of the present disclosure provides an organic light-emitting device. As shown in FIG. 2, the organic light-emitting device includes: a substrate 1, an anode 2 (ITO), a hole injection layer 3, a first hole transmission layer 4, a second hole transmission layer 5, a light-emitting layer 6, an electron transmission layer 7, an electron injection layer 8, a cathode 9 (magnesium-silver electrode, Mg to Ag mass ratio 9:1), and a capping layer (CPL) 10. The ITO anode 2 has a thickness of 15 nm, the hole injection layer 3 has a thickness of 5 nm, the first hole transmission layer 4 has a thickness of 100 nm, the second hole transmission layer 5 has a thickness of 5 nm, the light-emitting layer 6 has a thickness of 30 nm, the electron transmission layer 7 has a thickness of 30 nm, the electron injection layer 8 has a thickness of 5 nm, the magnesium-silver electrode 9 has a thickness of 10 nm, and the capping layer (CPL) 10 has a thickness of 100 nm.

Device Example 1

The present example provides an organic light-emitting device, which is specifically manufactured by the following steps:

1) A glass substrate was cut into a size of 50 mm×50 mm×0.7 mm, subjected to ultrasonic treatment respectively in isopropyl alcohol and in deionized water for 30 minutes, and then exposed to ozone for about 10 minutes for cleaning, so as to obtain the substrate 1. The obtained glass substrate with an indium tin oxide (ITO) anode 2 having a thickness of 15 nm was mounted on a vacuum deposition apparatus;

2) Compound 2 as a hole injection layer material and compound 1 as a p-dopant material, in a doping ratio of 3% by weight, were co-deposited by vacuum evaporation on the ITO anode layer 2, so as to form a hole injection layer 3 having a thickness of 5 nm;

3) Compound 3 as a hole transmission layer material was deposited by vacuum evaporation on the hole injection layer 3 to form a first hole transmission layer 4 having a thickness of 100 nm;

4) Compound 4 as the hole transmission material was deposited by vacuum evaporation on the first hole transmission layer 4 to form a second hole transmission layer 5 having a thickness of 5 nm;

5) Compound 5 as a host material, and compound 6 as a dopant, in a doping ratio of 3% by weight, were deposited by vacuum evaporation on the second hole transmission layer 5 to form a light-emitting layer 6 having a thickness of 30 nm;

6) Compound 7 as the electron transmission material was deposited by vacuum evaporation on the light-emitting layer 6 to form an electron transmission layer 7 having a thickness of 30 nm;

7) Compound 8 as an electron transmission material, and compound 9 as an n-dopant, in a doping mass ratio of 1:1, were deposited by vacuum evaporation on the electron transmission layer 7 to form an electron injection layer 8 having a thickness of 5 nm;

8) a magnesium and silver electrode (a ratio of Mg to Ag is 9:1) was deposited by vacuum evaporation on the electron injection layer 8 to form a cathode 9 having a thickness of 10 nm; and 9) Compound P1 of the present disclosure was deposited by vacuum evaporation on the cathode 9 to form a capping layer 10 having a thickness of 100 nm.

Device Example 2

Device Example 2 differs from Device Example 1 in that the compound P1 was replaced with compound P4.

Device Example 3

Device Example 3 differs from Device Example 1 in that the compound P1 was replaced with compound P29.

Device Example 4

Device Example 4 differs from Device Example 1 in that the compound P1 was replaced with compound P43.

Device Example 5

Device Example 5 differs from Device Example 1 in that the compound P1 was replaced with compound P66.

Device Comparative Example 1

Device Comparative Example 1 differs from Device Example 1 in that the compound P1 was replaced with compound A.

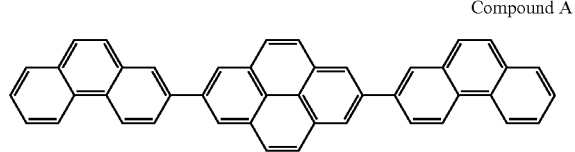 [SMILES: c1ccc2c(c1)ccc1cc(-c3cc4ccc5cc(-c6ccc7c(ccc8ccccc87)c6)cc6ccc(c3)c4c56)ccc12]

Compound A

Device Comparative Example 2

Device Comparative Example 2 differs from Device Example 1 in that the compound P1 was replaced with compound B.

Compound B

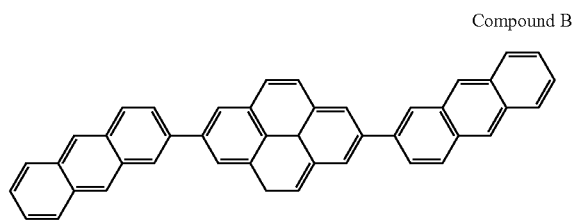 [SMILES: C1=Cc2cc(-c3ccc4cc5ccccc5cc4c3)cc3c2C2C(=CC3)C=C(c3ccc4cc5ccccc5cc4c3)C=C12]

Tests of Performances:

(1) The compounds, which was used as the capping layer in the device examples and the device comparative examples, were tested in terms of glass transition temperature $T_g$, the refractive index n, and the extinction coefficient k. The results are shown in Table 1. The glass transition temperature $T_g$ was measured by the differential scanning calorimetry (DSC, Waters Technology (Shanghai) Co., Ltd., PerkinElmer DSC 8000 Differential Scanning Calorimeter), with a heating rate of 10 C/mmn. The refractive index n and the extinction coefficient k were measured under atmospheric environment by an ellipsometer (J. A. Woollam Co., USA; Model: ALPHA-SE).

as the CPL materials, thereby improving the light extraction efficiency and the light-emitting efficiency of the display panel.

(2) Performance evaluation of organic light-emitting devices

A Keithley 2365A digital nanovoltmeter was used to measure the currents of the display panels manufactured according to the examples and comparative examples at different voltages. The currents were divided by the light-emitting area to calculate current densities of the organic light-emitting device at different voltages. Konicaminolta CS-2000 spectroradiometer was used to measure the brightness and the radiant energy flux density of organic light-emitting devices manufactured according to the examples and comparative examples at different voltages. According to the current densities and brightness of the organic light-emitting devices at different voltages, an operating voltage Von, a current efficiency (Cd/A), and an external quantum efficiency EQE under the same current density were obtained (10 mA/cm$^2$). The service life T95 was obtained by measuring a time period during which the brightness of the organic light-emitting device was reduced to 95% of an initial brightness (measured at 50 mA/cm$^2$).

The performance test results of the organic light-emitting devices are shown in Table 2.

TABLE 1

| No. | Compound | $T_g$/° C. | 450 nm n | 450 nm k | 550 nm n | 550 nm k | 630 nm n | 630 nm k |
|---|---|---|---|---|---|---|---|---|
| Device Example 1 | P1 | 160 | 2.28 | 0.028 | 2.14 | 0.000 | 2.01 | 0.000 |
| Device Example 2 | P4 | 167 | 2.46 | 0.030 | 2.24 | 0.000 | 2.13 | 0.000 |
| Device Example 3 | P29 | 161 | 2.45 | 0.030 | 2.12 | 0.000 | 2.09 | 0.000 |
| Device Example 4 | P43 | 162 | 2.23 | 0.008 | 2.10 | 0.000 | 2.00 | 0.000 |
| Device Example 5 | P66 | 159 | 2.20 | 0.016 | 2.14 | 0.000 | 2.02 | 0.000 |
| Device Example 6 | P67 | 156 | 2.32 | 0.012 | 2.13 | 0.000 | 2.00 | 0.000 |
| Device Comparative Example 1 | Compound A | 140 | 2.02 | 0.027 | 1.85 | 0.000 | 1.79 | 0.000 |
| Device Comparative Example 2 | Compound B | 136 | 1.98 | 0.031 | 1.81 | 0.000 | 1.68 | 0.000 |

As can be seen from Table 1 above, for visible light having a wavelength of 450-630 nm, the refractive indexes of the compounds P1, P4, P29, P43, P66, and P67 of the present disclosure are all greater than 1.9, satisfying the refractive index requirements on the CPL of the light-emitting devices. Compared with compound A and compound B, the CPL materials of the present disclosure have higher refractive indexes. In addition, the glass transition temperatures of the compounds P1, P4, P29, P43, P66, and P67 of the present disclosure are all higher than 150° C. That is, the compounds of the present disclosure have high thermal stability, and thus the organic light-emitting device has a longer service life. Further, the extinction coefficient k of the compounds of the present disclosure is smaller than or equal to 0.05, and thus the compounds are suitable to be used

TABLE 2

| No. | CPL material | Drive voltage (V) | CE (cd/A) | Service life LT95 |
|---|---|---|---|---|
| Device Example 1 | P1 | 3.69 | 6.4 | 72 |
| Device Example 2 | P4 | 3.62 | 7.4 | 69 |
| Device Example 3 | P29 | 3.69 | 6.8 | 68 |
| Device Example 4 | P43 | 3.68 | 6.7 | 67 |
| Device Example 5 | P66 | 3.66 | 6.5 | 70 |
| Device Example 6 | P67 | 3.81 | 6.4 | 65 |
| Device Comparative Example 1 | Compound A | 4.05 | 5.3 | 57 |
| Device Comparative Example 2 | Compound B | 4.40 | 4.8 | 49 |

As can be seen from Table 2 above, the light-emitting devices using the compounds of the present disclosure as the CPL material having much lower drive voltages than the comparative devices, indicating that the compounds of the present disclosure can effectively reduce the power consumption of the light-emitting device. Compared with the comparative device, the current efficiencies of the light-emitting devices using the compound of the present disclosure as the CPL material are significantly improved.

Figure 3:
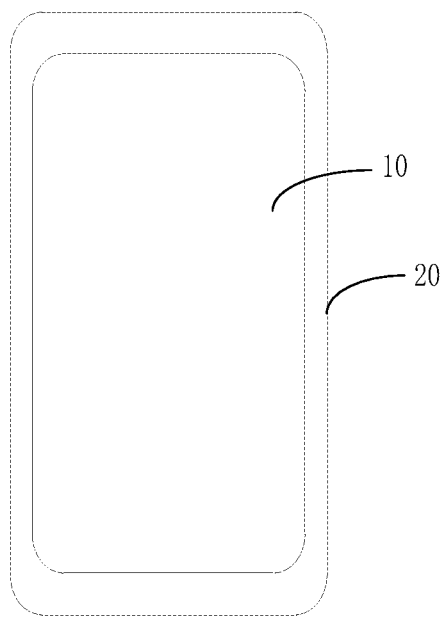
FIG. 3 is a schematic diagram of a display apparatus according to an embodiment of the present disclosure.

The present disclosure further provides a display apparatus including the organic light-emitting display panel described above. The organic light-emitting device of the present disclosure may be an OLED used in an organic light-emitting display apparatus. The organic light-emitting display apparatus may be a display screen of mobile phone, computer, TV, smart watch, smart car, VR or AR helmet, or other smart devices. FIG. 3 is a schematic diagram of a display apparatus according to an embodiment of the present disclosure. In FIG. 3, a mobile phone display panel is denoted with 10, and a display apparatus is denoted with 20.

What is claimed is:

1. A compound, having a structure represented by chemical formula 1:

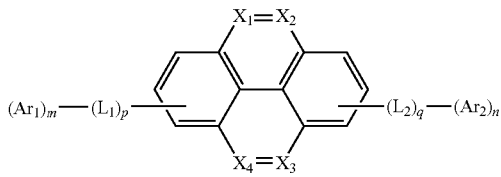

Chemical Formula 1 wherein $X_1$-$X_4$ are each independently a nitrogen atom or C—$R_a$, one or two of $X_1$-$X_4$ are a nitrogen atom, when one of $X_1$ and $X_2$ is a nitrogen atom, the other one of $X_1$ and $X_2$ is not N;

when one of $X_3$ and $X_4$ is a nitrogen atom, the other one of $X_3$ and $X_4$ is not N;

$R_a$ is selected from the group consisting of hydrogen, deuterium, fluorine, a substituted or unsubstituted C1-C20 alkyl, a substituted or unsubstituted C1-C20 thioalkyl, a substituted or unsubstituted C6-C30 aryl, and a substituted or unsubstituted C3-C30 heteroaryl;

$R_a$ is present independently or forms, with adjacent carbon atoms, a substituted or unsubstituted aliphatic ring, a substituted or unsubstituted aromatic ring, or a substituted or unsubstituted heteroaromatic ring;

$Ar_1$ and $Ar_2$ are each independently selected from the group consisting of a substituted or unsubstituted phenyl, a substituted or unsubstituted biphenyl, a substituted or unsubstituted triphenyl, a substituted or unsubstituted tetraphenyl, a substituted or unsubstituted naphthyl, a substituted or unsubstituted anthryl, a substituted or unsubstituted phenanthryl, a substituted or unsubstituted pyrenyl, a substituted or unsubstituted spirobifluorenyl, a substituted or unsubstituted carbazolyl, a substituted or unsubstituted dibenzofuryl, a substituted or unsubstituted dibenzothienyl, a substituted or unsubstituted pyrimidinyl, a substituted or unsubstituted triazinyl, a substituted or unsubstituted indolocarbazolyl, a substituted or unsubstituted indolobenzofuryl, a substituted or unsubstituted indolobenzothienyl, a substituted or unsubstituted benzofurylpyrimidinyl, and a substituted or unsubstituted benzothienylpyrimidinyl;

m and n are each an integer independently selected from 0, 1, 2, or 3, and when one of m and n is 0, the other one of m and n is not 0;

$L_1$ and $L_2$ are each independently a single bond, a substituted or unsubstituted C6-C30 arylene, or a substituted or unsubstituted C3-C30 heteroarylene; and p and q are each an integer independently selected from 0, 1, or 2.

2. The compound according to claim 1, wherein $X_1$ and $X_3$ are each a nitrogen atom, and $X_2$ and $X_4$ are C—$R_a$; or $X_1$ and $X_4$ are each a nitrogen atom, and $X_2$ and $X_3$ are C—$R_a$, wherein $R_a$ is H.

3. The compound according to claim 1, wherein $X_1$ and $X_3$ are each a nitrogen atom, and $X_2$ and $X_4$ are C—$R_a$; or $X_1$ and $X_4$ are each a nitrogen atom, and $X_2$ and $X_3$ are C—$R_a$, wherein $R_a$ is methyl.

4. The compound according to claim 1, wherein $Ar_1$ and $Ar_2$ are each independently selected from the group consisting of phenyl, biphenyl, triphenyl, tetraphenyl, spirobifluorenyl, naphthyl, pyrrolyl, furyl, thienyl, indolyl, benzofuryl, benzothienyl, carbazolyl, dibenzofuryl, dibenzothienyl, indenocarbazolyl, indolocarbazolyl, pyridyl, pyrimidinyl, pyrazinyl, pyridazinyl, triazinyl, phenanthryl, triphenylenyl, and combinaitons thereof.

5. The compound according to claim 1, wherein the substituted or unsubstituted phenyl is o-biphenyl, m-biphenyl, or p-biphenyl;

the substituted or unsubstituted biphenyl is o-triphenyl, m-triphenyl, or p-triphenyl;

the substituted or unsubstituted triphenyl is o-tetraphenyl, m-tetraphenyl, or p-tetraphenyl;

the substituted or unsubstituted spirobifluorenyl is 1-spirobifluorenyl, 2-spirobifluorenyl, 3-spirobifluorenyl, or 4-spirobifluorenyl;

the substituted or unsubstituted naphthyl is 1-naphthyl, or 2-naphthyl;

the substituted or unsubstituted carbazolyl is 1-carbazolyl, 2-carbazolyl, 3-carbazolyl, or 4-carbazolyl;

the substituted or unsubstituted dibenzofuryl is 1-dibenzofuryl, 2-dibenzofuryl, 3-dibenzofuryl, or 4-dibenzofuryl;

the substituted or unsubstituted dibenzothienyl is 1-dibenzothienyl, 2-dibenzothienyl, 3-dibenzothienyl, or 4-dibenzothienyl;

the substituted or unsubstituted pyridyl is 2-pyridyl, 3-pyridyl, or 4-pyridyl; and the substituted or unsubstituted pyrimidinyl is 2-pyrimidinyl, 4-pyrimidinyl, or 5-pyrimidinyl.

6. The compound according to claim 1, wherein $Ar_1$ and $Ar_2$ are each independently selected from the group consisting of naphthyl, anthryl, phenanthryl, and pyrenyl; and $L_1$ and $L_2$ are each a single bond.

7. A compound, wherein the compound is any one of the following compounds:
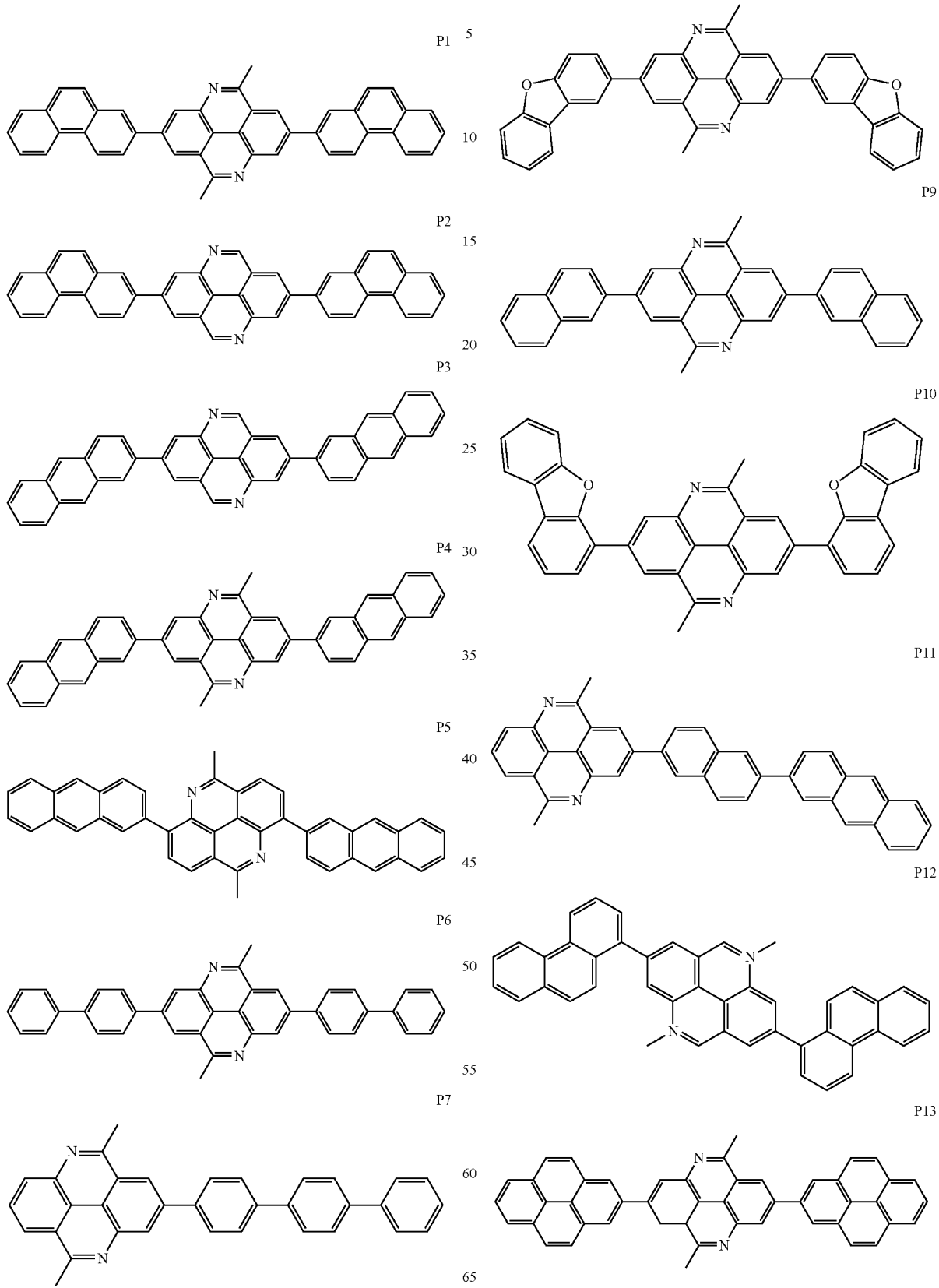

P14
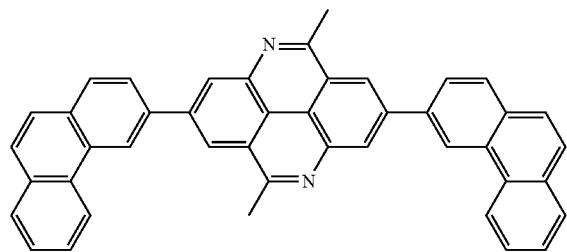
P15
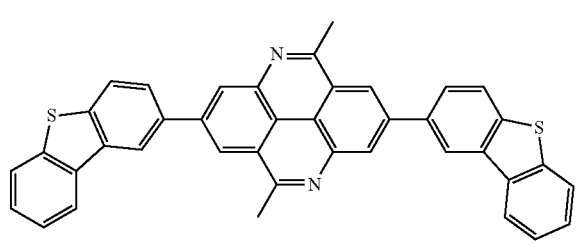
P16
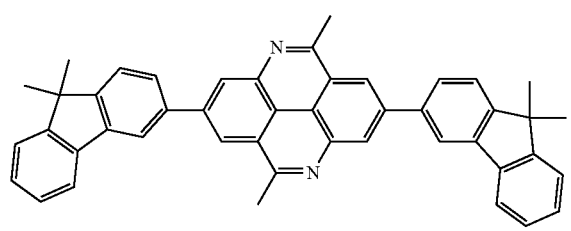
P17
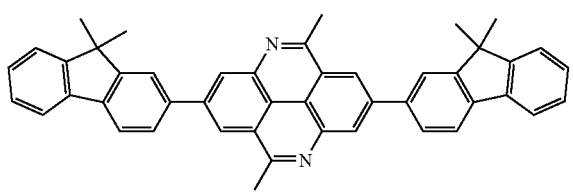
P18
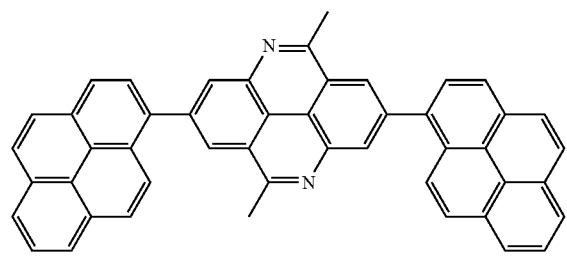
P19
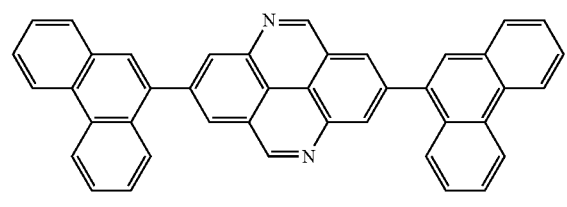
P20
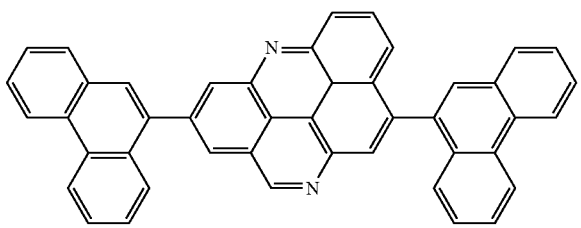
P21
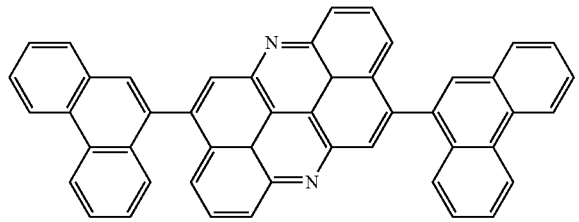
P22
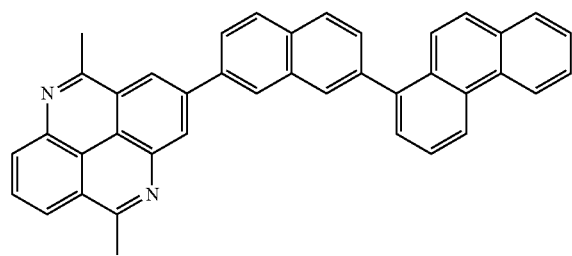
P23
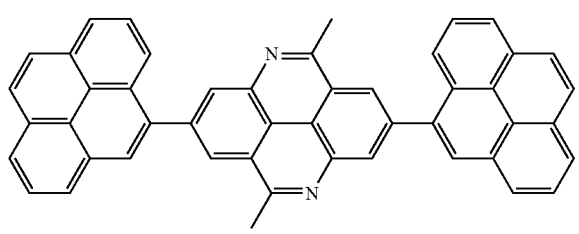
P24
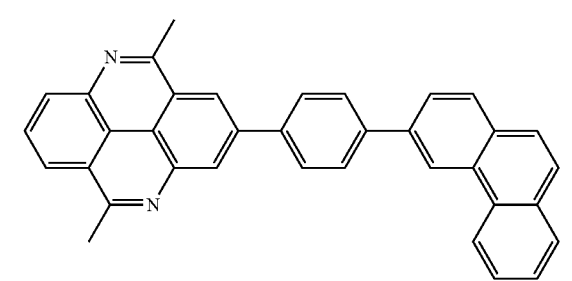

P25
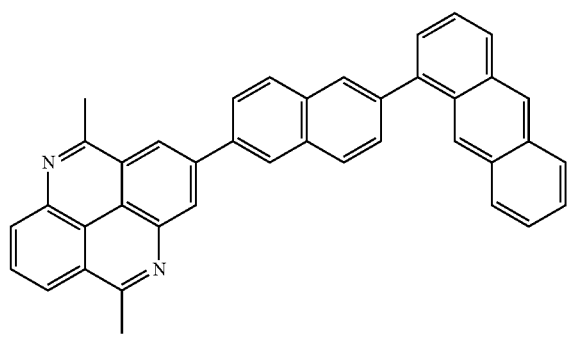
P26
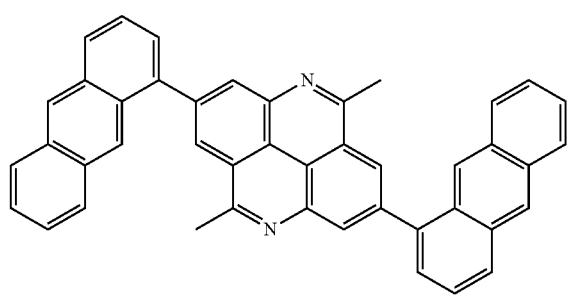
P27
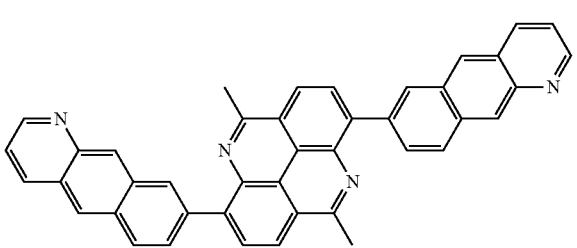
P28
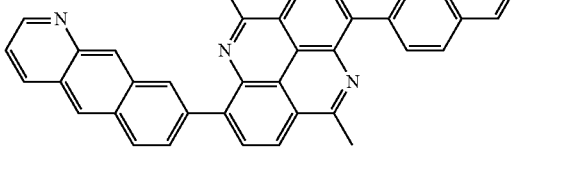
P29
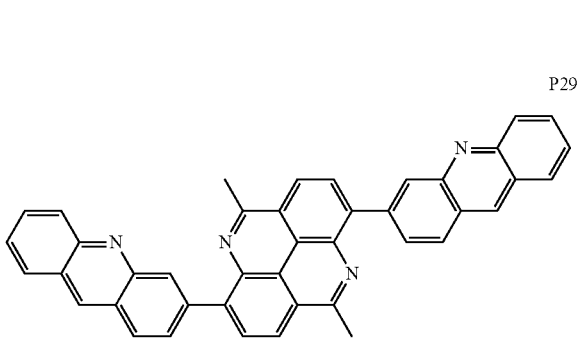
P30
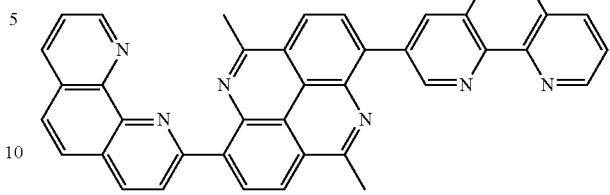
P31
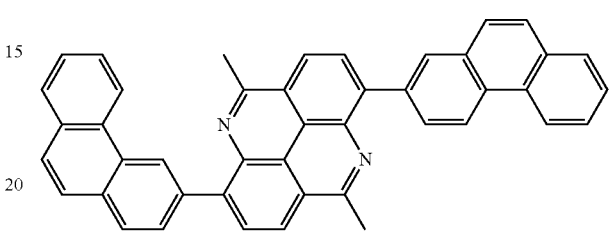
P32
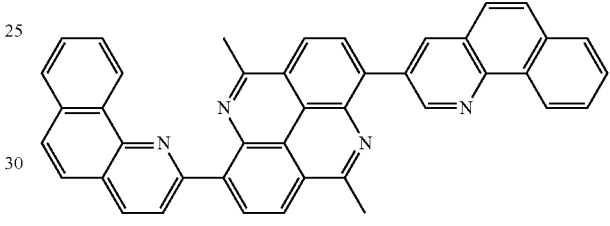
P33
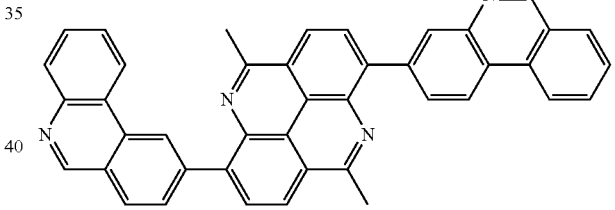
P34
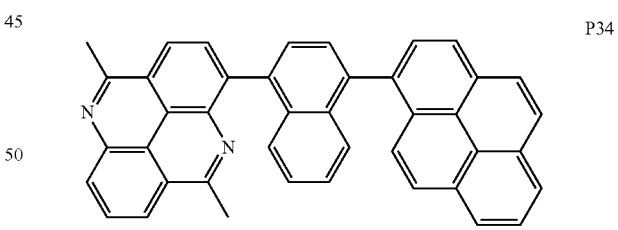
P35
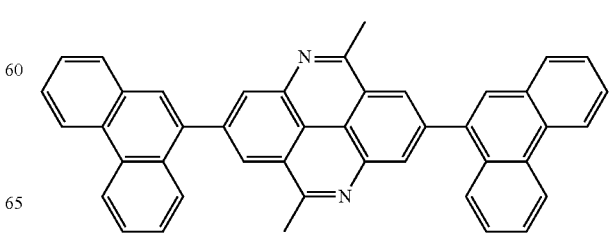

-continued
P36
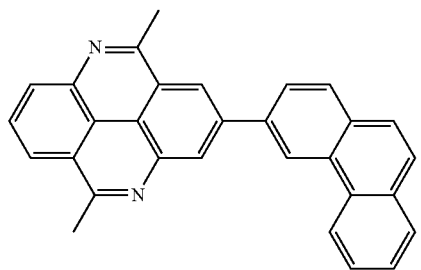
P37
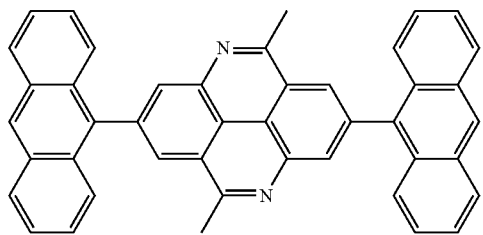
P38
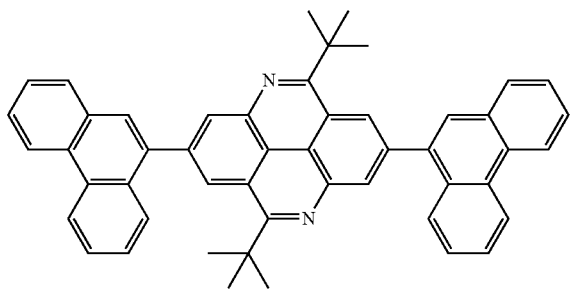
P39
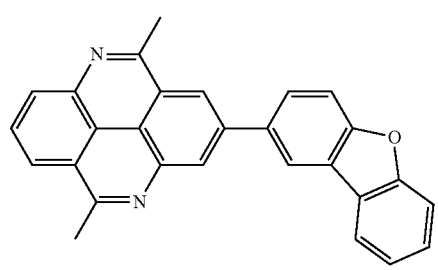
P40
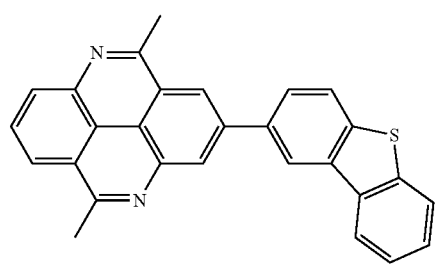
P41
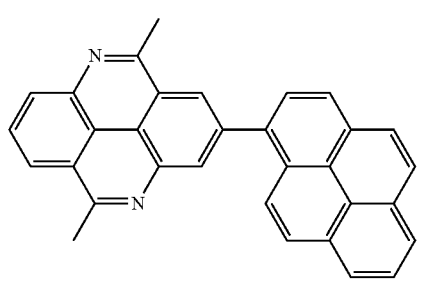
P42
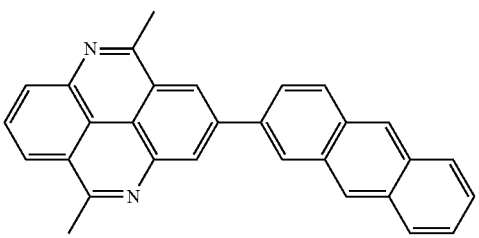
P43
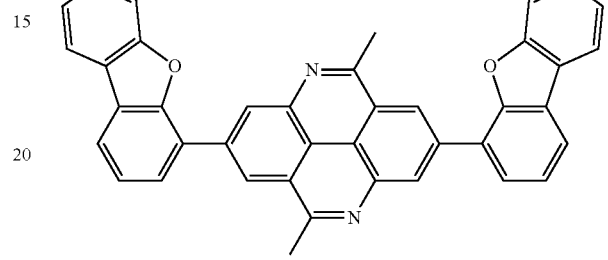
P44
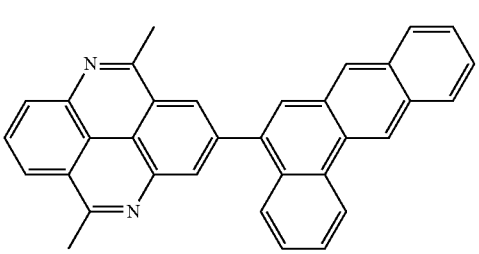
P45
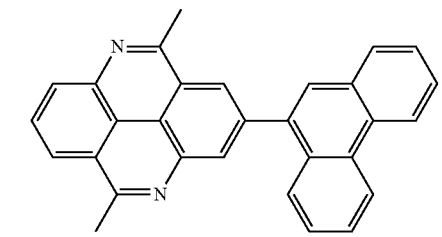
P46
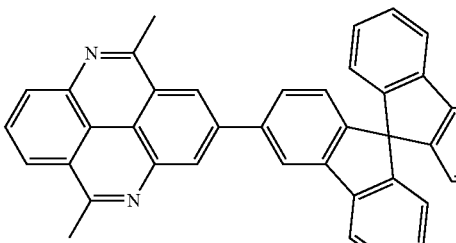
P47
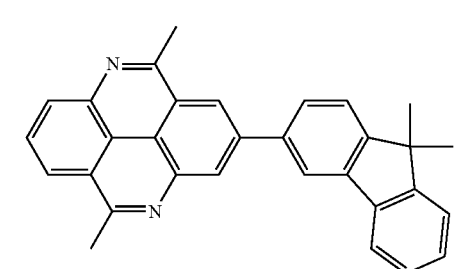

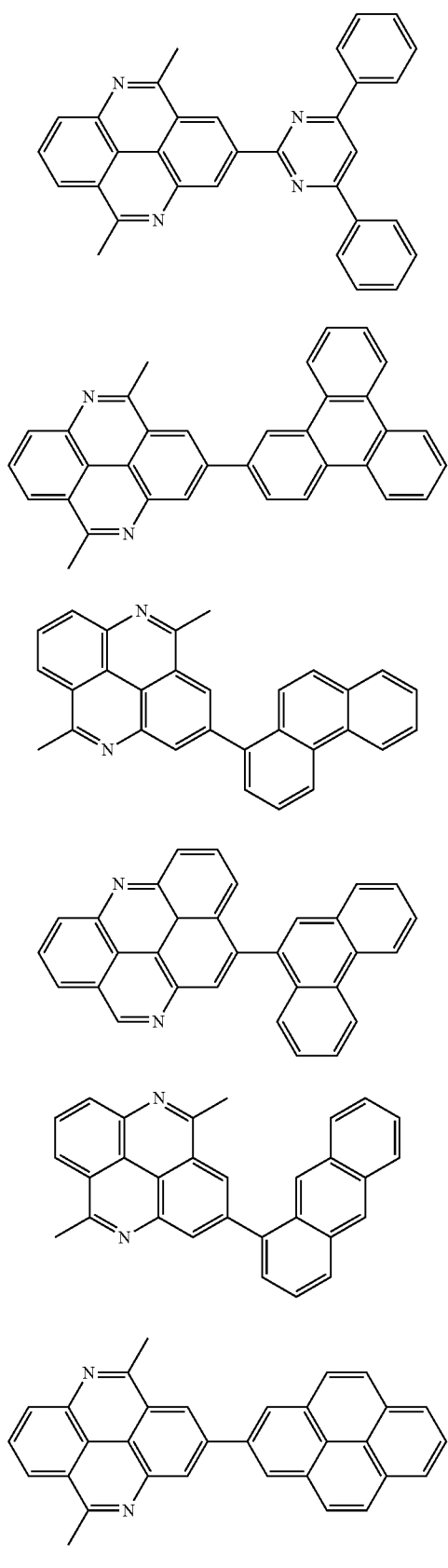
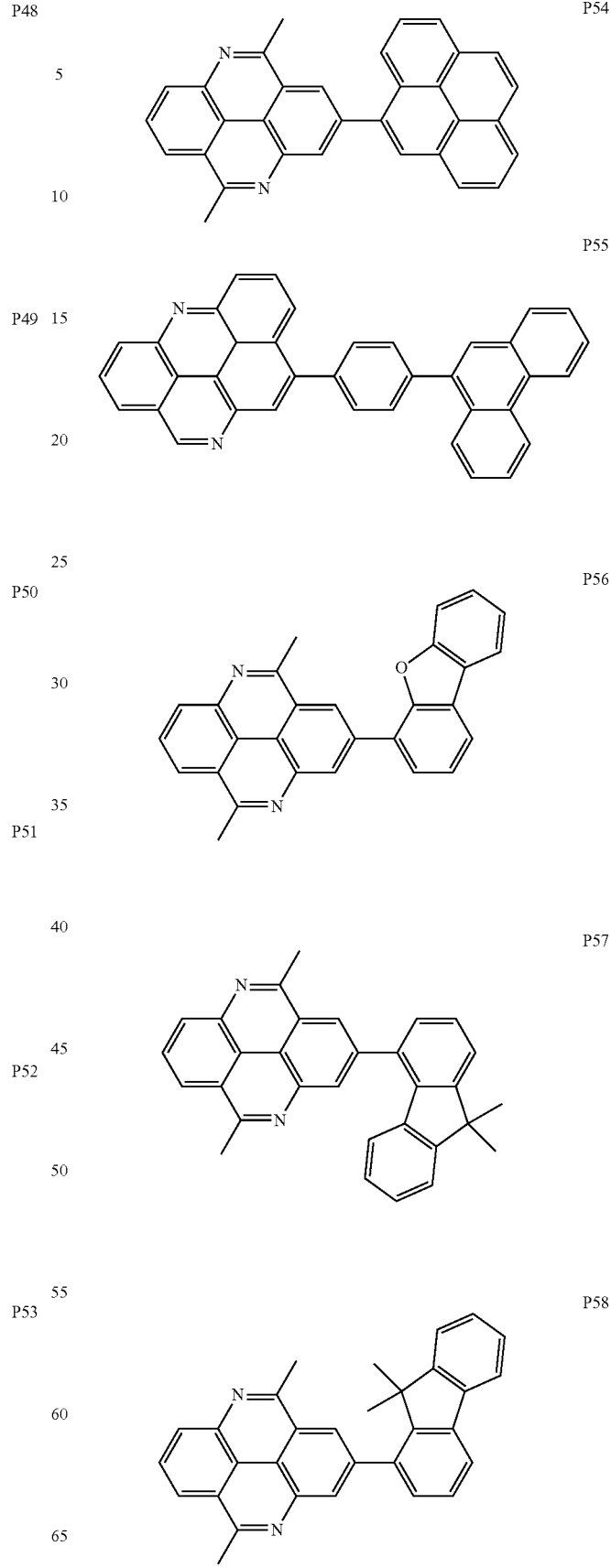

-continued
P59
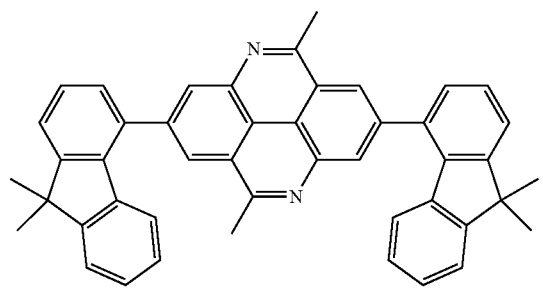
P60
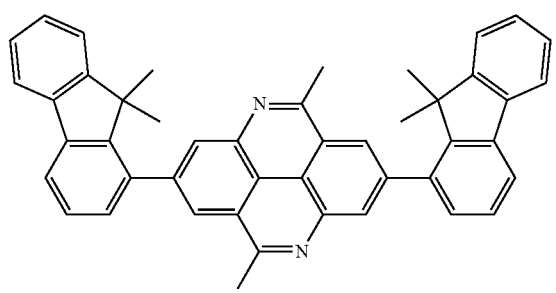
P61
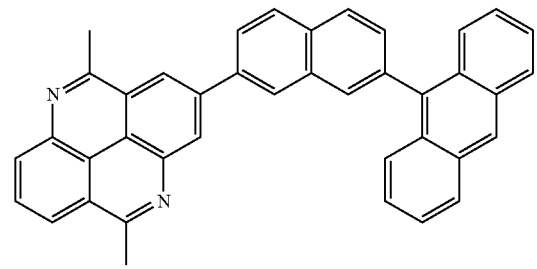
P62
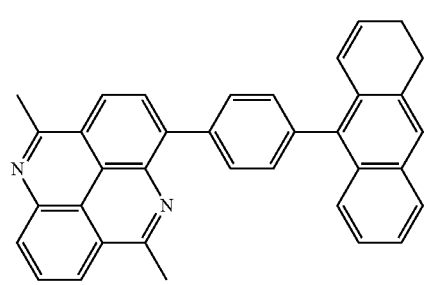
P63
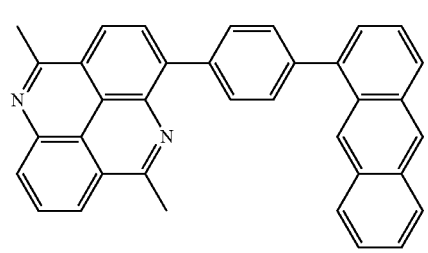
-continued
P64
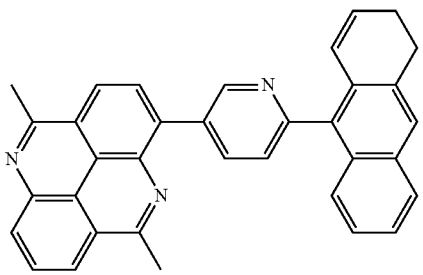
P65
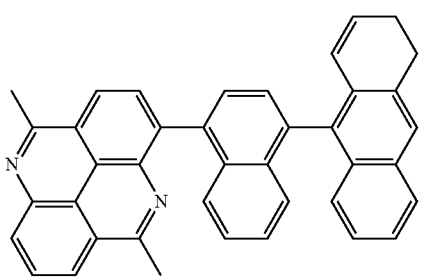
P66
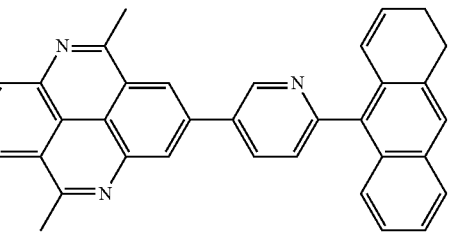
P67
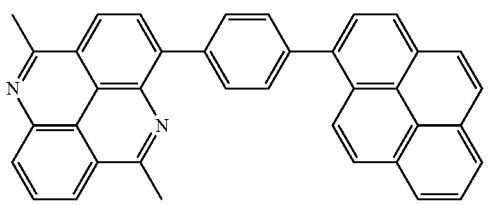
P68
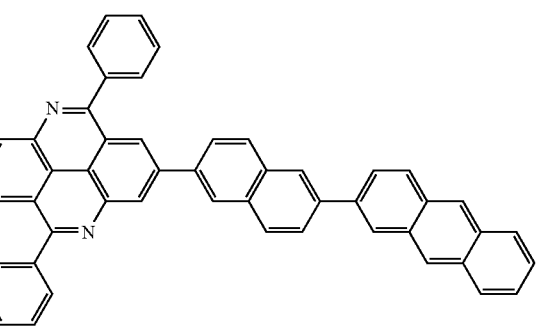

P69

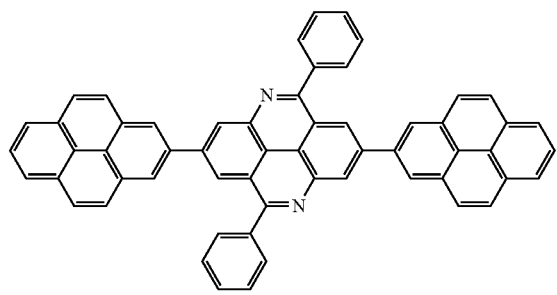

P70

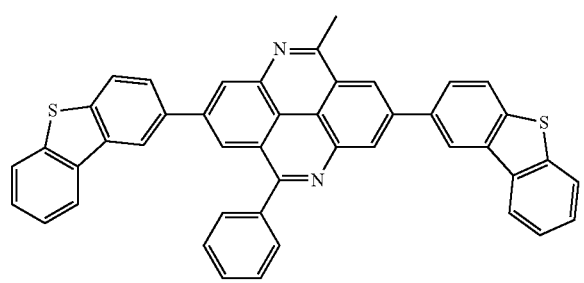

P71

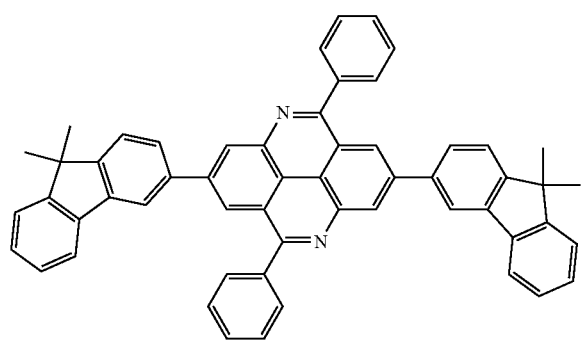

P72

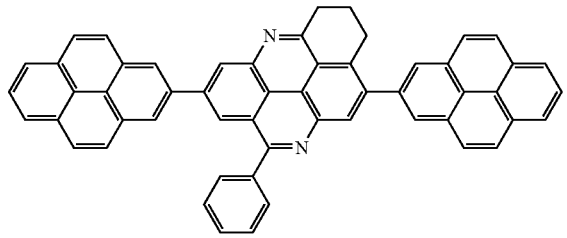

P73

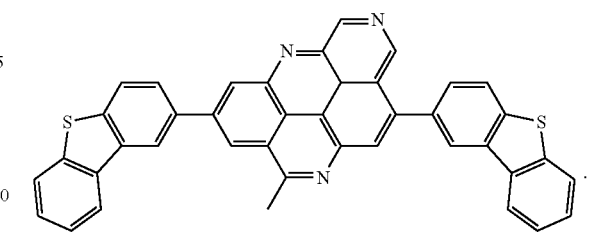

8. The compound according to claim 1, wherein the compound has a refractive index n greater than or equal to 2.0 for visible light having a wavelength of 400 nm to 700 nm.

9. The compound according to claim 1, wherein the compound has an extinction coefficient k smaller than or equal to 0.05 for visible light having a wavelength of 400 nm to 450 nm.

10. A display panel, comprising an organic light-emitting device,
the organic light-emitting device comprising:
an anode;
a cathode arranged opposite to the anode;
a capping layer located a side of the cathode facing away from the anode; and
an organic layer located between the anode and the cathode,
wherein the organic layer comprises a light-emitting layer, and a material of the capping layer comprises the compound according to claim 1.

11. The display panel according to claim 10, wherein the cathode with the capping layer has a transmittance greater than or equal to 65% for visible light having a wavelength of 400 nm to 700 nm.

12. A display apparatus comprising the display panel according to claim 10.

13. The compound according to claim 7, wherein the compound has a refractive index n greater than or equal to 2.0 for visible light having a wavelength of 400 nm to 700 nm.

14. The compound according to claim 7, wherein the compound has an extinction coefficient k smaller than or equal to 0.05 for visible light having a wavelength of 400 nm to 450 nm.

* * * * *